US009232933B2

United States Patent
Oaks et al.

(10) Patent No.: US 9,232,933 B2
(45) Date of Patent: Jan. 12, 2016

(54) TRANSFORMER-BASED MULTIPLEXER FOR ULTRASOUND IMAGING SYSTEM AND METHOD

(71) Applicants: KABUSHIKI KAISHA TOSHIBA, Tokyo (JP); TOSHIBA MEDICAL SYSTEMS CORPORATION, Otawara-Shi, Tochigi-Ken (JP)

(72) Inventors: David Oaks, Tacoma, WA (US); Daniel Brueske, Sammamish, WA (US)

(73) Assignees: KABUSHIKI KAISHA TOSHIBA, Tokyo (JP); TOSHIBA MEDICAL SYSTEMS CORPORATION, Otawara-Shi (JP)

( * ) Notice: Subject to any disclaimer, the term of this patent is extended or adjusted under 35 U.S.C. 154(b) by 533 days.

(21) Appl. No.: 13/757,092

(22) Filed: Feb. 1, 2013

(65) Prior Publication Data
US 2014/0221839 A1    Aug. 7, 2014

(51) Int. Cl.
*A61B 8/14* (2006.01)
*A61B 8/00* (2006.01)
*G01S 7/52* (2006.01)

(52) U.S. Cl.
CPC ... *A61B 8/42* (2013.01); *A61B 8/44* (2013.01); *G01S 7/52017* (2013.01); *A61B 8/4477* (2013.01)

(58) Field of Classification Search
CPC ........ A61B 8/42; A61B 8/406; A61B 8/4477; A61B 8/44; G01S 7/52017
See application file for complete search history.

(56) References Cited

U.S. PATENT DOCUMENTS

| 3,919,683 | A | * | 11/1975 | Itamura | A61B 8/00 367/103 |
| 4,222,274 | A | * | 9/1980 | Johnson | A61B 8/0825 128/915 |
| 5,151,085 | A | * | 9/1992 | Sakurai | A61B 8/546 310/316.02 |
| 5,495,765 | A | * | 3/1996 | Dykes | B06B 1/0215 367/99 |
| 6,050,945 | A | * | 4/2000 | Peterson | B06B 1/0215 600/443 |
| 6,083,164 | A | | 7/2000 | Oppelt et al. | |
| 6,229,455 | B1 | * | 5/2001 | Yost | G07F 17/24 340/932.2 |
| 2003/0158478 | A1 | * | 8/2003 | Petersen | H04L 25/4917 600/437 |
| 2005/0243650 | A1 | | 11/2005 | Petersen et al. | |
| 2006/0084859 | A1 | * | 4/2006 | Johnson | A61B 5/0507 600/407 |
| 2007/0239001 | A1 | * | 10/2007 | Mehi | G01S 7/52017 600/437 |

* cited by examiner

*Primary Examiner* — Laura Martin
*Assistant Examiner* — Rose M Miller
(74) *Attorney, Agent, or Firm* — Yoshida & Associates, LLC

(57) ABSTRACT

A low-loss high-voltage multiplexer is implemented using a transformer that is connected to one transmitter, one receiver and transducer elements. At least one primary winding is magnetically coupled at least two secondary windings. For example, a first transducer element and a second transducer element are connected to the secondary windings of a multiplexer that multiplexes between these transducer elements via the secondary windings. The multiplexer also optionally switches between the transmitter and the receiver during the transmission and the reception.

28 Claims, 13 Drawing Sheets

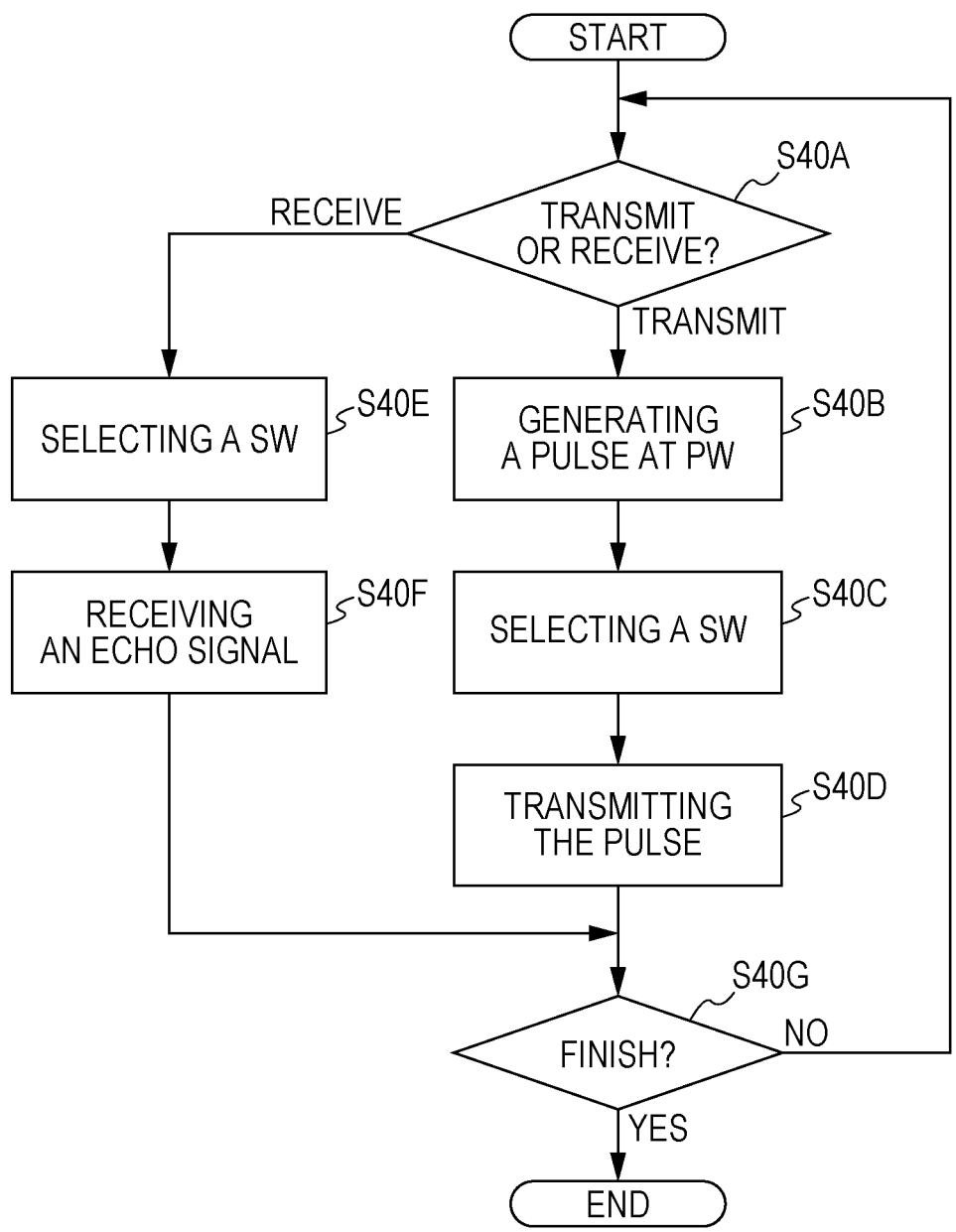

TRANSFORMER-BASED MULTIPLEXER FOR ULTRASOUND IMAGING SYSTEM AND METHOD

FIELD OF THE INVENTION

The current invention is generally related to ultrasound imaging systems and methods, and more particularly related to a transformer-based multiplexer for controlling signals during transmission and or reception.

BACKGROUND OF THE INVENTION

Some prior-art ultrasound front-end circuits disclose an automatic controller for switching between the transmit mode and the receive mode. One exemplary device is a transformer-based transmitter with an integrated transmit/receive (TR) switch for switching between transmission and reception. Other prior-art transformer-based transmitters used multiple poles in the transformer to generate transmission signals at multiple output levels. In any case, a transfer is utilized as a TR switch and or a multi-level output generator.

Unfortunately, when a transformer was used in prior art attempts, high voltage loss and or high power loss is experienced in the high voltage transformer or the associated components such as a switch. Thus, it remains desirable to implement a high voltage transformer with a low voltage loss and a low power loss to be used in an ultrasound imaging system. In addition to the TR switch function and the multi-level output generator function, it is also desired that a transformer performs an additional function such as multiplexing among the transducer elements.

BRIEF DESCRIPTION OF THE DRAWINGS

FIG. 13 is a flow chart illustrating certain steps or acts involved in changing modes in an embodiment or a process of multiplexing at least two transducer elements using a transfer-based multiplexer in an ultrasound imaging system according to the current invention.

DETAILED DESCRIPTION OF THE PREFERRED EMBODIMENT(S)

Figure 1:
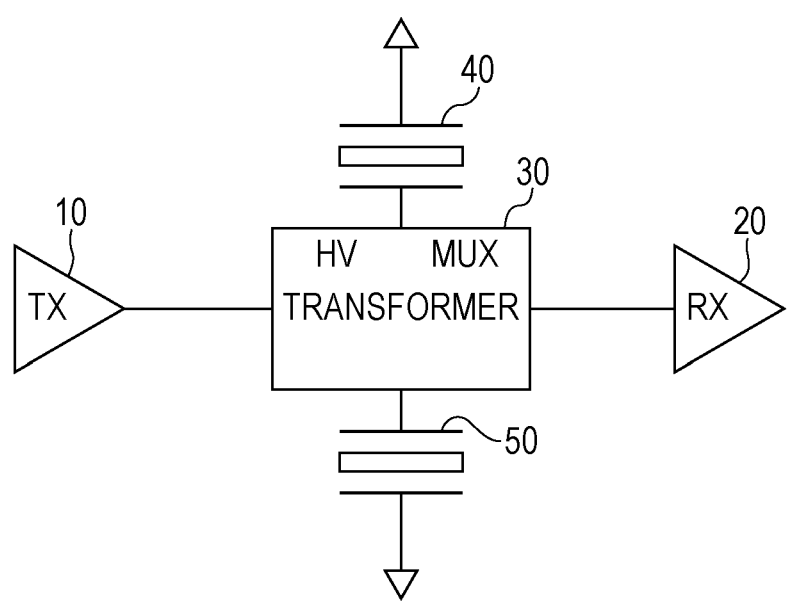
FIG. 1 illustrates one embodiment including one transmitter and one receiver that are connected to a low-loss high-voltage multiplexer using a transformer according to the current invention.

In general, a low-loss and high-voltage multiplexer is implemented in various embodiments using a transformer according to the current invention for an ultrasound imaging system. The transformer is connected to at least two transducer elements that are selected or multiplexed for transmitting one of the predetermined ultrasound signals into a region of interest. The same transformer is also connected to at least a receiver component that selectively processes ultrasound echo signals in a predetermined multiplexed manner. One embodiment in the ultrasound front-end circuit takes advantage of transformer properties, and the windings are constructed to implement the low-loss and high-voltage multiplexer function. The windings include at least one primary winding, at least one secondary winding and at least one third winding. Although these windings are magnetically coupled according to the basis of transformer principles, their electrical configurations associated with each of the windings are constructed according to the current invention.

In a core of the transformer, at least the primary winding such as a first winding is magnetically coupled with at least two secondary windings such as a second winding and a third winding in one embodiment of the multiplexer according to the current invention. Furthermore, the at least two windings are formed on separate poles so that they are magnetically isolated with each other. In the one embodiment of the transformer according to the current invention, the at least one first winding is connected to a transmitter for sending one of the predetermined signals. The second winding is magnetically coupled with the first winding while it is connected to one of at least two transducer elements. By the same token, the third winding is magnetically coupled with the first winding while it is connected to the other one of the at least two transducer elements. On the other hand, the third winding is magnetically isolated from the second winding. In the one embodiment of the transformer according to the current invention, a second shorting device is associated with the second winding for being selectively activated to shorting the second winding while the second winding is electronically isolated from the first winding. Similarly, a third shorting device is associated with the third winding for being selectively activated to shorting the third winding while the third winding is electronically isolated from the first winding and the second winding.

The activation of the selected winding is accompanied by deactivating or shorting the other one winding or other unselected windings using a corresponding shorting device. The shoring device includes a shorting winding that is associated with a corresponding secondary winding. For example, when the shorting winding is grounded at both ends, the associated secondary winding is no longer coupled to the primary winding. In another example, the shorting device includes an active switch and or a passive switch that is optionally associated with the secondary windings.

Referring now to the drawings, wherein like reference numerals designate corresponding structures throughout the views, and referring in particular to FIG. 1, one transmitter 10 and one receiver 20 are connected to one embodiment of a low-loss high-voltage multiplexer 30 that is implemented on a transformer according to the current invention. A first transducer element 40 and a second transducer element 50 are also connected to the low-loss high-voltage multiplexer 30 in the embodiment according to the current invention. The low-loss high-voltage multiplexer 30 switches between the transmitter 10 and the receiver 20. Similarly, the low-loss high-voltage multiplexer 30 also switches between the first transducer element 40 and the second transducer element 50 during the transmission and the reception. The low-loss high-voltage multiplexer 30 will be further described in detail and its alternative embodiment will be also provided in the following.

Figure 2A:
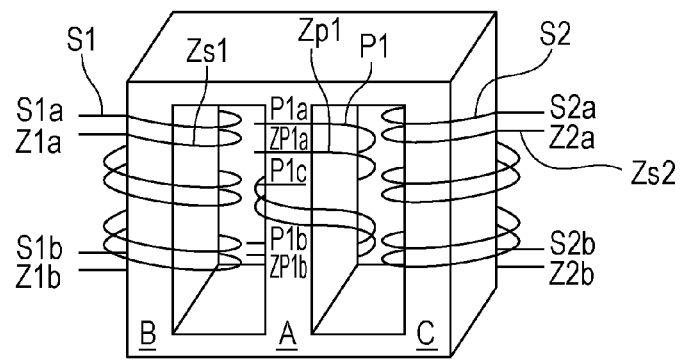
FIG. 2A is a diagram illustrating a transformer core to be used in a first embodiment of the multiplexer according to the current invention.

Now referring to FIG. 2A, a diagram illustrates a transformer core to be used in a first embodiment of the multiplexer according to the current invention. A primary winding P1 on a first pole A has endings P1$a$ and P1$b$ as well as a tapping terminal P1$c$. A first shorting winding Zp1 also on the first pole A has endings Zp1$a$ and Zp1$b$ and is magnetically associated with the primary winding P1. A first secondary winding S1 on a second pole B has endings S1$a$ and S1$b$ and is magnetically coupled with the primary winding P1. A first secondary shorting winding Zs1 also on the second pole B is magnetically coupled with the first secondary winding S1 and has endings Z1$a$ and Z1$b$. A second secondary winding S2 on a third pole C has endings S2$a$ and S2$b$ and is magnetically coupled with the primary winding P1. A second secondary shorting winding Zs2 also on the third pole C is magnetically coupled with the second secondary winding S2 and has endings Z2$a$ and Z2$b$. Although the first secondary winding S1 and the second secondary winding S2 are magnetically associated with the primary winding P1, the first secondary winding S1 and the second secondary winding S2 are not magnetically coupled with each other since the poles B and C are provided in a such manner to prevent magnetic coupling. The relative physical locations of the poles A, B and C are merely conceptual and are not limited to the illustrated relation.

Figure 2B:
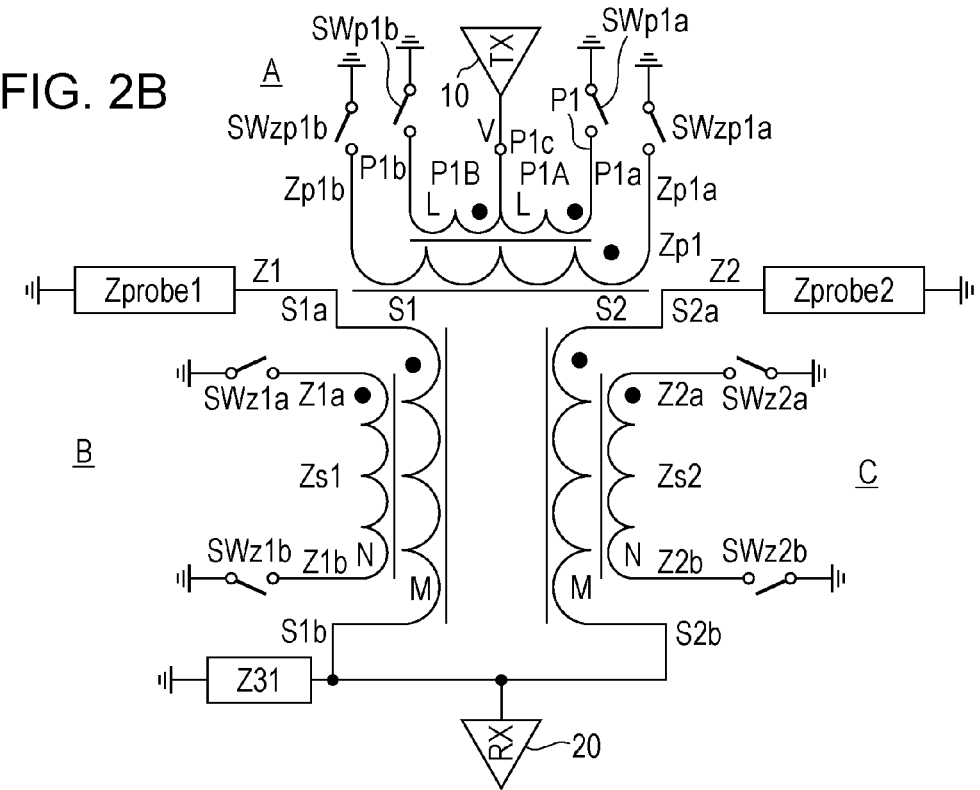
FIG. 2B is a diagram illustrating connections in the transformer-based multiplexer and with the associated components in the first embodiment of the ultrasound imaging system according to the current invention.

Now referring to FIG. 2B, a diagram illustrates connections in the transformer-based multiplexer and with the associated components in the first embodiment of the ultrasound imaging system according to the current invention. The primary winding P1 and the first shorting winding ZP1 are magnetically coupled on the pole A. The primary winding P1 has two subsections P1A and P1B, and the transmitter TX 10 is tapped in at the terminal P1$c$ between the two subsections P1A and P1B. The primary winding P1 has the terminals P1$a$ and P1$b$, which are respectively connected to switches SWp1$a$ and SWp1$b$ that are in turn grounded. By turning on and off SWp1$a$ and SWp1$b$, a pulse is generated according the transmitter signal from the transmitter TX 10. The first shorting winding ZP1 has the terminals Zp1$a$ and Zp1$b$, which are respectively connected to switches SWzp1$a$ and SWzp1$b$ that are in turn grounded. By closing the switches SWzp1$a$ and SWzp1$b$, the primary winding P1 is no longer magnetically coupled to other windings as will be later described in detail.

The first secondary winding S1 on the second pole B has the endings S1$a$ and S1$b$ and is magnetically coupled with the primary winding P1. The ending S1$a$ is connected to Zprobe1 such as a transducer element Z1 while the ending S1$b$ is connected to an impedance Z31 and the receiver 20. The first secondary shorting winding Zs1 also on the second pole B is magnetically coupled with the first secondary winding S1 and has the endings Z1a and Z1b, which are respectively connected to switches SWz1a and SWz1b that are in turn grounded. By closing the switches SWz1a and SWz1b, the first secondary winding S1 is no longer magnetically coupled to the primary winding P1 and consequently receives none of the pulsed waveforms from the primary winding P1.

The second secondary winding S2 on the third pole C has the endings S2a and S2b and is magnetically coupled with the primary winding P1. The ending S2a is connected to Zprobe2 such as a transducer element Z2 while the ending S2b is connected to an impedance Z31, which is connected to the receiver 20. The second secondary shorting winding Zs2 also on the third pole C is magnetically coupled with the second secondary winding S2 and has endings Z2a and Z2b, which are respectively connected to switches SWz2a and SWz2b that are in turn grounded. By closing the switches SWz2a and SWz2b, the second secondary winding S2 is no longer magnetically coupled to the primary winding P1 and consequently receives none of the pulsed waveforms from the primary winding P1.

In the above embodiment of the transformer-based multiplexer, the windings are constructed in a certain manner. Although the first secondary winding S1 and the second secondary winding S2 are magnetically associated with the primary winding P1 in an independent manner, the first secondary winding S1 and the second secondary winding S2 are not magnetically coupled with each other since the poles B and C are provided in a such manner to prevent magnetic coupling. Furthermore, the secondary windings S1 and S2 are electrically isolated from each other for implementing the high-voltage (HV) multiplexer.

The above described ultrasound front-end circuit containing the transformer-based multiplexer has two predetermined modes of operation including transmit (TX) and receive (RX). A transmission/receive (TR) switch is implemented using the switches SWzp1a and SWzp1b in combination with an impedance Z31. When both of the switches SWzp1a and SWzp1b are closed, the first shorting winding Zp1 is grounded and the primary winding P1 is no longer magnetically active. On the other hand, when either of the switches SWzp1a and SWzp1b is open, the first shorting winding Zp1 is not grounded and the primary winding P1 is magnetically active to couple with the first secondary winding S1 and or the second secondary winding S2 for transmitting a pulse signal to a transducer element. Thus, by not grounding the first shorting winding Zp1, the primary winding P1 functionally switches the front-end circuit into the TX mode. In contrast, when both of the switches SWzp1a and SWzp1b are closed, the ultrasound front-end circuit is in the RX mode since no pulse signal is outputted to either of the secondary windings S1/S2 since the primary winding P1 is not magnetically active.

During the TX mode, by turning on and off the switches SWp1a and SWp1b, a pulsed signal or waveform is generated at the primary winding P1 according to a transmitter signal from the transmitter 10 and is outputted through the primary winding P1 to one of the secondary windings S1 and S2 that are selectively coupled to the primary winding P1. Also during the TX mode, the secondary shorting windings ZS1 and ZS2 are used to determine which of Zprobe1 or Zprobe2 impedance is connected via the selected one of the secondary windings S1 and S2 so as to receive the pulsed waveform. That is, either one of the secondary shorting windings ZS1 and ZS2 is alternately grounded by closing only one corresponding pair of the switches SWz2a/SWz2b and the switches SWz1a/SWz1b according to the transmitter signal from the transmitter 10. Consequently, the pulsed signal from the primary winding P1 is outputted to Zprobe1 or Zprobe2 at a time via a selected one of the secondary windings S1 and S2 whose associated secondary shorting winding ZS1 or ZS2 is not grounded.

During the receive (RX) mode, the receiver 20 is selectively connected to the summation of two output nodes via the secondary windings S1 and S2. To receive one echo signal from a transducer element via either one of the secondary windings S1 and S2, a corresponding one of the two pairs of the switches SWz1a/SWz1b and SWz2a/SWz2b is closed depending on which probe impedance was selected during the TX mode. That is, by shorting the secondary shorting winding ZS1 or ZS2, the associated grounded secondary winding provides a low impedance path for the echo signal to travel as an input to the receiver 20. At the same time, the other one of the two pairs of the switches SWz1a/SWz1b and SWz2a/SWz2b is kept open so that an echo signal from the other one of the secondary windings S1 and S2 does not interfere with the input to the receiver 20. Impedance Z31 is used to short one side of winding so that a voltage develops across one of the selected secondary windings S1 and S2. The impedance Z31 is also used to protect the input of the receiver 20.

Figure 2C:
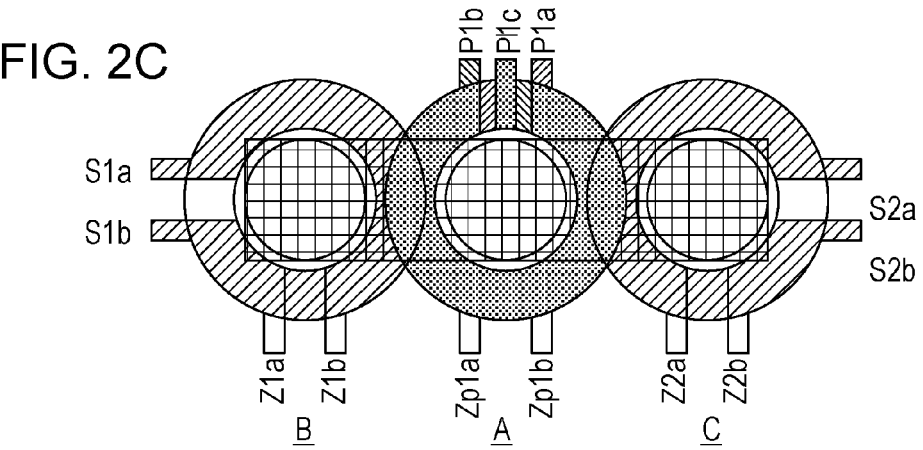
FIG. 2C is a diagram illustrating a cross sectional view of the core of the transformer-based multiplexer in the first embodiment of the current invention.

Now referring to FIG. 2C, a diagram illustrates a cross sectional view of the core of the transformer-based multiplexer in one embodiment of the current invention. On the pole A, the primary winding P1 and the first shorting winding Zp1 are placed at a predetermined ratio. The primary winding P1 has its endings P1a and P1b as well as its tapping point P1c while the first shorting winding Zp1 has its endings Zp1a and Zp1b. By the same token, on the pole B, the first secondary winding S1 and the first secondary shorting winding Zs1 are placed at a predetermined ratio. The first secondary winding S1 has its endings S1a and S1b while the first secondary shorting winding Zs1 has its endings Z1a and Z1b. On the pole C, the second secondary winding S2 and the second secondary shorting winding Zs2 are placed at a predetermined ratio. The second secondary winding S2 has its endings S2a and S2b while the second secondary shorting winding Zs2 has its endings Z2a and Z2b. The pole A is located between the poles B and C so that the secondary windings S1 and S2 are magnetically isolated with each other. On the other hand, the poles B and C are adjacent to the pole A so that the secondary windings S1 and S2 are each magnetically coupled to the primary winding P1. Although the embodiment aligns the poles A, B and C in a straight line, it is not limited to the illustrated configuration.

Figure 3A:
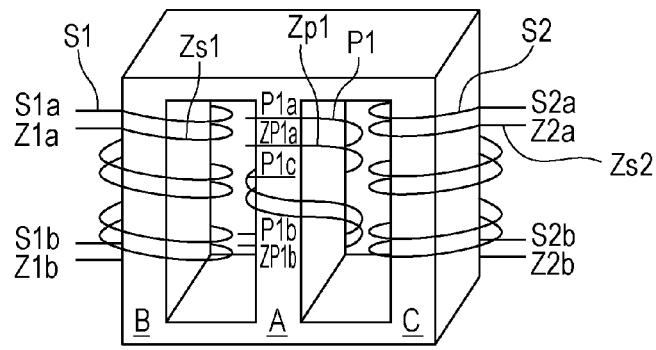
FIG. 3A is a diagram illustrating a transformer core to be used in a second embodiment of the multiplexer according to the current invention.

Now referring to FIG. 3A, a diagram illustrates a transformer core to be used in a second embodiment of the multiplexer according to the current invention. A primary winding P1 on a first pole A has endings P1a and P1b as well as a tapping terminal P1c. A first shorting winding Zp1 also on the first pole A has endings Zp1a and Zp1b and is magnetically associated with the primary winding P1. A first secondary winding S1 on a second pole B has endings S1a and S1b and is magnetically coupled with the primary winding P1. A first secondary shorting winding Zs1 also on the second pole B is magnetically coupled with the first secondary winding S1 and has endings Z1a and Z1b. A second secondary winding S2 on a third pole C has endings S2a and S2b and is magnetically coupled with the primary winding P1. A second secondary shorting winding Zs2 also on the third pole C is magnetically coupled with the second secondary winding S2 and has endings Z2a and Z2b. Although the first secondary winding S1 and the second secondary winding S2 are magnetically associated with the primary winding P1, the first secondary winding S1 and the second secondary winding S2 are not magnetically coupled with each other since the poles B and C are provided in a such manner to prevent magnetic coupling. The relative physical locations of the poles A, B and C are merely conceptual and are not limited to the illustrated relation.

Figure 3B:
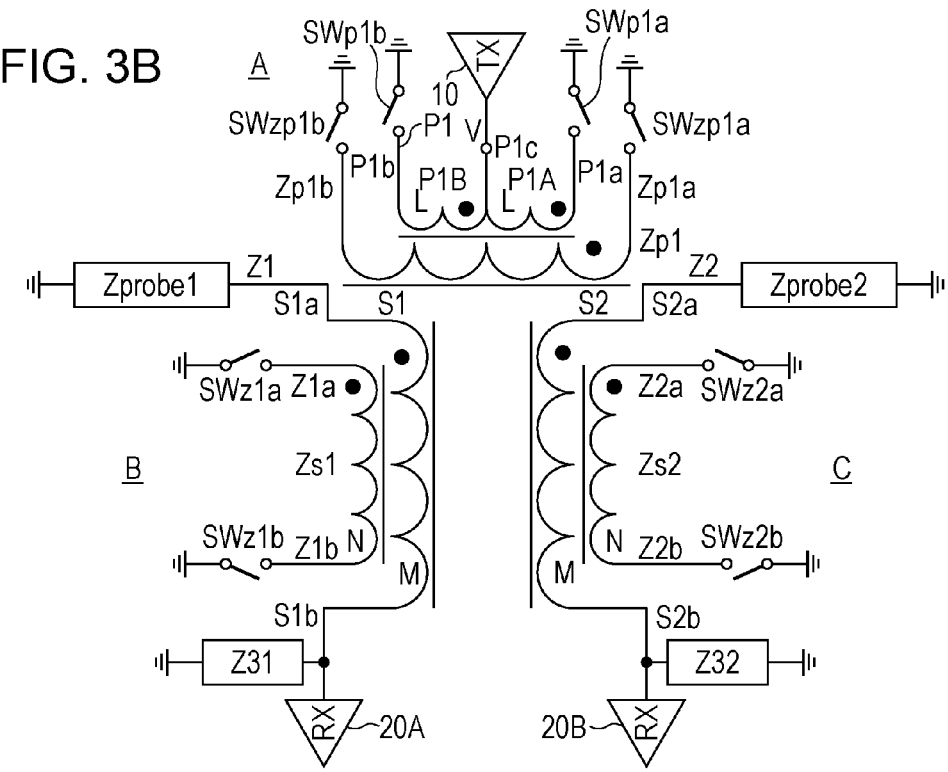
FIG. 3B is a diagram illustrating connections in the transformer-based multiplexer and with the associated components in the second embodiment of the ultrasound imaging system according to the current invention.

Now referring to FIG. 3B, a diagram illustrates connections in the transformer-based multiplexer and with the associated components in the second embodiment of the ultrasound imaging system according to the current invention. The primary winding P1 and the first shorting winding ZP1 are magnetically coupled on the pole A. The primary winding P1 has two subsections P1A and P1B, and the transmitter TX 10 is tapped in at the terminal P1C between the two subsections P1A and P1B. The primary winding P1 has the terminals P1$a$ and P1$b$, which are respectively connected to switches SWp1$a$ and SWp1$b$ that are in turn grounded. By turning on and off SWp1$a$ and SWp1$b$, a pulse is generated according the transmitter signal from the transmitter TX 10. The first shorting winding ZP1 has the terminals Zp1$a$ and Zp1$b$, which are respectively connected to switches SWzp1$a$ and SWzp1$b$ that are in turn grounded. By closing the switches SWzp1$a$ and SWzp1$b$, the primary winding P1 is no longer magnetically coupled to other windings as will be later described in detail.

The first secondary winding S1 on the second pole B has the endings S1$a$ and S1$b$ and is magnetically coupled with the primary winding P1. The ending S1$a$ is connected to Zprobe1 such as a transducer element Z1 while the ending S1$b$ is connected to an impedance Z31 and a first receiver RX 20A. The first secondary shorting winding Zs1 also on the second pole B is magnetically coupled with the first secondary winding S1 and has the endings Z1$a$ and Z1$b$, which are respectively connected to switches SWz1$a$ and SWz1$b$ that are in turn grounded. By closing the switches SWz1$a$ and SWz1$b$, the first secondary winding S1 is no longer magnetically coupled to the primary winding P1 and consequently receives none of the pulsed waveforms from the primary winding P1.

The second secondary winding S2 on the third pole C has the endings S2$a$ and S2$b$ and is magnetically coupled with the primary winding P1. The ending S2$a$ is connected to Zprobe2 such as a transducer element Z2 while the ending S2$b$ is connected to an impedance Z32 and a second receiver RX 20B. The second secondary shorting winding Zs2 also on the third pole C is magnetically coupled with the second secondary winding S2 and has endings Z2$a$ and Z2$b$, which are respectively connected to switches SWz2$a$ and SWz2$b$ that are in turn grounded. By closing the switches SWz2$a$ and SWz2$b$, the second secondary winding S2 is no longer magnetically coupled to the primary winding P1 and consequently receives none of the pulsed waveforms from the primary winding P1.

In the above embodiment of the transformer-based multiplexer, the windings are constructed in a certain manner. Although the first secondary winding S1 and the second secondary winding S2 are magnetically associated with the primary winding P1 in an independent manner, the first secondary winding S1 and the second secondary winding S2 are not magnetically coupled with each other since the poles B and C are provided in a such manner to prevent magnetic coupling. Furthermore, the secondary windings S1 and S2 are electrically isolated from each other for implementing the high-voltage (HV) multiplexer.

The above described ultrasound front-end circuit containing the transformer-based multiplexer has two predetermined modes of operation including transmit (TX) and receive (RX). A transmission/receive (TR) switch is implemented using the switches SWzp1$a$ and SWzp1$b$ in combination with the impedance units Z31 and Z32. When both of the switches SWzp1$a$ and SWzp1$b$ are closed, the first shorting winding Zp1 is grounded and the primary winding P1 is no longer magnetically active. On the other hand, when either of the switches SWzp1$a$ and SWzp1$b$ is open, the first shorting winding Zp1 is not grounded and the primary winding P1 is magnetically active to couple with the first secondary winding S1 and or the second secondary winding S2 for transmitting a pulse signal to a transducer element. Thus, by not grounding the first shorting winding Zp1, the primary winding P1 functionally switches the front-end circuit into the TX mode. In contrast, when both of the switches SWzp1$a$ and SWzp1$b$ are closed, the ultrasound front-end circuit is in the RX mode since no pulse signal is outputted to either of the secondary windings S1/S2 since the primary winding P1 is not magnetically active.

During the TX mode, by turning on and off the switches SWp1$a$ and SWp1$b$, a pulsed signal or waveform is generated at the primary winding P1 according to a transmitter signal from the transmitter TX 10 and is outputted through the primary winding P1 to one of the secondary windings S1 and S2 that are selectively coupled to the primary winding P1. Also during the TX mode, the secondary shorting windings ZS1 and ZS2 are used to determine which of Zprobe1 or Zprobe2 impedance is connected via the selected one of the secondary windings S1 and S2 so as to receive the pulsed waveform. That is, either one of the secondary shorting windings ZS1 and ZS2 is alternately grounded by closing only one corresponding pair of the switches SWz2$a$/SWz2$b$ and the switches SWz1$a$/SWz1$b$ according to the transmitter signal from the transmitter TX 10. Consequently, the pulsed signal from the primary winding P1 is outputted to Zprobe1 or Zprobe2 at a time via a selected one of the secondary windings S1 and S2 whose associated secondary shorting winding ZS1 or ZS2 is not grounded.

During the receive (RX) mode, either one of the receivers RX 20A and 20B is selectively connected to the two independent output nodes via the secondary winding S1 or S2. To receive one echo signal from a transducer element via either one of the secondary windings S1 and S2, a corresponding one of the two pairs of the switches SWz1$a$/SWz1$b$ and SWz2$a$/SWz2$b$ is closed depending on which probe impedance was selected during the TX mode. That is, by shorting the secondary shorting winding ZS1 or ZS2, the associated grounded secondary winding provides a low impedance path for the echo signal to travel as an input to the receiver 20A or 20B. At the same time, the other one of the two pairs of the switches SWz1$a$/SWz1$b$ and SWz2$a$/SWz2$b$ is optionally kept open. Since the path to the receiver 20A or 20B is independent, an echo signal from the other one of the secondary windings S1 and S2 does not interfere with the input to the receiver 20. Impedance components Z31 and Z32 are used to short a corresponding side of the winding so that a voltage develops across one of the selected secondary windings S1 and S2. The impedance components Z31 and Z32 are also used to protect the input of the receivers RX 20A and 20B.

Figure 3C:
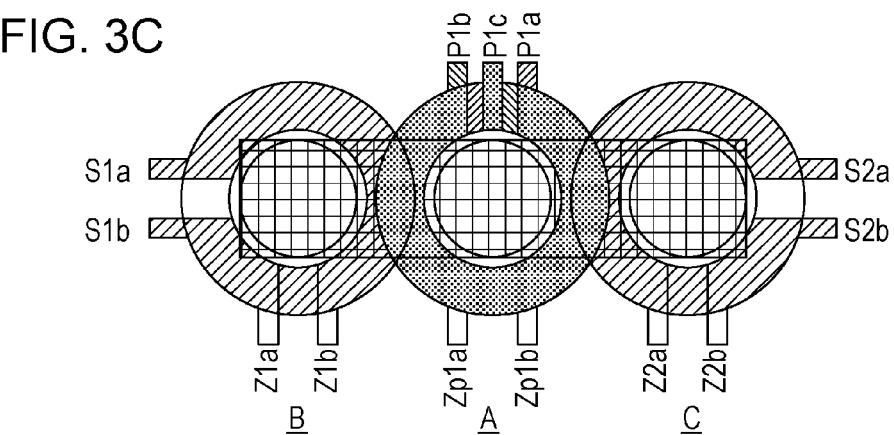
FIG. 3C is a diagram illustrating a cross sectional view of the core of the transformer-based multiplexer in the second embodiment of the current invention.

Now referring to FIG. 3C, a diagram illustrates a cross sectional view of the core of the transformer-based multiplexer in one embodiment of the current invention. On the pole A, the primary winding P1 and the first shorting winding Zp1 are placed at a predetermined ratio. The primary winding P1 has its endings P1$a$ and P1$b$ as well as its tapping point P1$c$ while the first shorting winding Zp1 has its endings Zp1$a$ and Zp1$b$. By the same token, on the pole B, the first secondary winding S1 and the first secondary shorting winding Zs1 are placed at a predetermined ratio. The first secondary winding S1 has its endings S1a and S1b while the first secondary shorting winding Zs1 has its endings Z1a and Z1b. On the pole C, the second secondary winding S2 and the second secondary shorting winding Zs2 are placed at a predetermined ratio. The second secondary winding S2 has its endings S2a and S2b while the second secondary shorting winding Zs2 has its endings Z2a and Z2b. The pole A is located between the poles B and C so that the secondary windings S1 and S2 are magnetically isolated with each other. On the other hand, the poles B and C are adjacent to the pole A so that the secondary windings S1 and S2 are each magnetically coupled to the primary winding P1. Although the embodiment aligns the poles A, B and C in a straight line, it is not limited to the illustrated configuration.

Figure 4A:
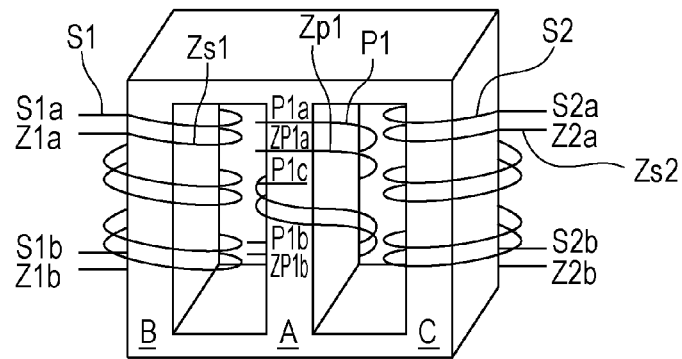
FIG. 4A is a diagram illustrating a transformer core to be used in a third embodiment of the multiplexer according to the current invention.

Now referring to FIG. 4A, a diagram illustrating a transformer core to be used in a third embodiment of the multiplexer according to the current invention. A primary winding P1 on a first pole A has endings P1a and P1b as well as a tapping terminal P1c. A first shorting winding Zp1 also on the first pole A has endings Zp1a and Zp1b and is magnetically associated with the primary winding P1. A first secondary winding S1 on a second pole B has endings S1a and S1b and is magnetically coupled with the primary winding P1. A first secondary shorting winding Zs1 also on the second pole B is magnetically coupled with the first secondary winding S1 and has endings Z1a and Z1b. A second secondary winding S2 on a third pole C has endings S2a and S2b and is magnetically coupled with the primary winding P1. A second secondary shorting winding Zs2 also on the third pole C is magnetically coupled with the second secondary winding S2 and has endings Z2a and Z2b. Although the first secondary winding S1 and the second secondary winding S2 are magnetically associated with the primary winding P1, the first secondary winding S1 and the second secondary winding S2 are not magnetically coupled with each other since the poles B and C are provided in a such manner to prevent magnetic coupling. The relative physical locations of the poles A, B and C are merely conceptual and are not limited to the illustrated relation.

Figure 4B:
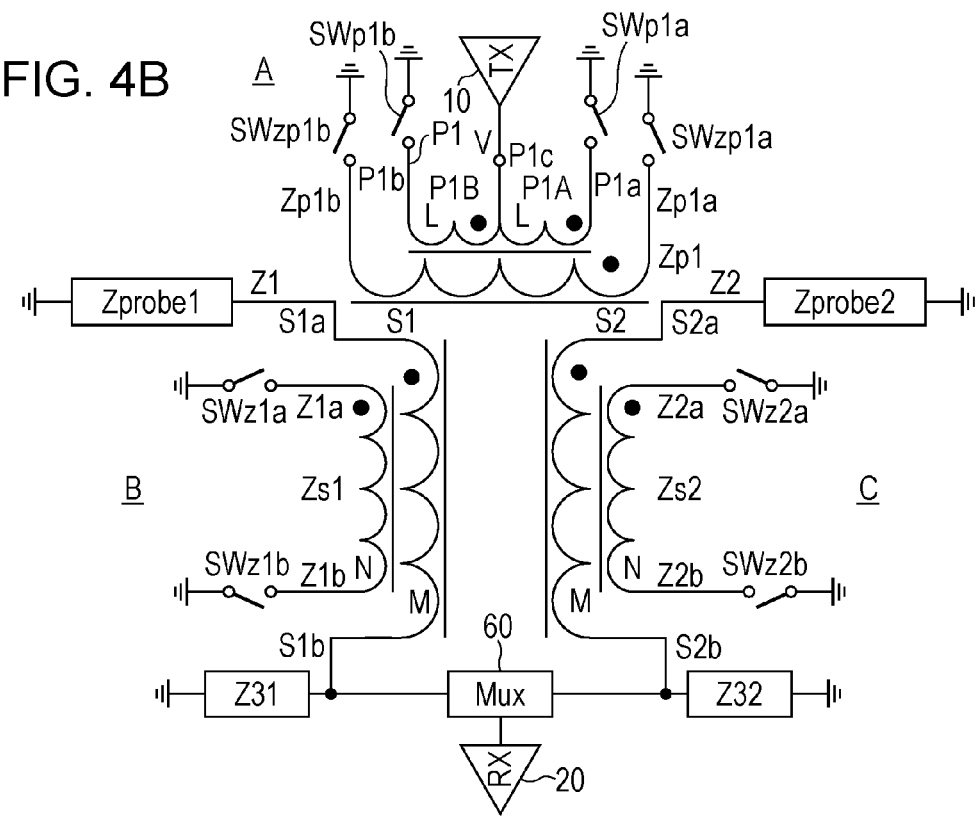
FIG. 4B is a diagram illustrating connections in the transformer-based multiplexer and with the associated components in the third embodiment of the ultrasound imaging system according to the current invention.

Now referring to FIG. 4B, a diagram illustrates connections in the transformer-based multiplexer and with the associated components in the third embodiment of the ultrasound imaging system according to the current invention. The primary winding P1 and the first shorting winding ZP1 are magnetically coupled on the pole A. The primary winding P1 has two subsections P1A and P1B, and the transmitter TX 10 is tapped in at the terminal P1c between the two subsections P1A and P1B. The primary winding P1 has the terminals P1a and P1b, which are respectively connected to switches SWp1a and SWp1b that are in turn grounded. By turning on and off SWp1a and SWp1b, a pulse is generated according the transmitter signal from the transmitter TX 10. The first shorting winding ZP1 has the terminals Zp1a and Zp1b, which are respectively connected to switches SWzp1a and SWzp1b that are in turn grounded. By closing the switches SWzp1a and SWzp1b, the primary winding P1 is no longer magnetically coupled to other windings as will be later described in detail.

The first secondary winding S1 on the second pole B has the endings S1a and S1b and is magnetically coupled with the primary winding P1. The ending S1a is connected to Zprobe1 such as a transducer element Z1 while the ending S1b is connected to an impedance component Z31 and the receiver 20 via a low-voltage multiplexer 60. The first secondary shorting winding Zs1 also on the second pole B is magnetically coupled with the first secondary winding S1 and has the endings Z1a and Z1b, which are respectively connected to switches SWz1a and SWz1b that are in turn grounded. By closing the switches SWz1a and SWz1b, the first secondary winding S1 is no longer magnetically coupled to the primary winding P1 and consequently receives none of the pulsed waveforms from the primary winding P1.

The second secondary winding S2 on the third pole C has the endings S2a and S2b and is magnetically coupled with the primary winding P1. The ending S2a is connected to Zprobe2 such as a transducer element Z2 while the ending S2b is connected to an impedance Z32 and the receiver 20 via the common low-voltage multiplexer 60. The second secondary shorting winding Zs2 also on the third pole C is magnetically coupled with the second secondary winding S2 and has endings Z2a and Z2b, which are respectively connected to switches SWz2a and SWz2b that are in turn grounded. By closing the switches SWz2a and SWz2b, the second secondary winding S2 is no longer magnetically coupled to the primary winding P1 and consequently receives none of the pulsed waveforms from the primary winding P1.

In the above embodiment of the transformer-based multiplexer, the windings are constructed in a certain manner. Although the first secondary winding S1 and the second secondary winding S2 are magnetically associated with the primary winding P1 in an independent manner, the first secondary winding S1 and the second secondary winding S2 are not magnetically coupled with each other since the poles B and C are provided in a such manner to prevent magnetic coupling. Furthermore, the secondary windings S1 and S2 are electrically isolated from each other for implementing the high-voltage (HV) multiplexer.

The above described ultrasound front-end circuit containing the transformer-based multiplexer has two predetermined modes of operation including transmit (TX) and receive (RX). A transmission/receive (TR) switch is implemented using the switches SWzp1a and SWzp1b in combination with the multiplexer 60 and the impedance components Z31 and Z32. When both of the switches SWzp1a and SWzp1b are closed, the first shorting winding Zp1 is grounded and the primary winding P1 is no longer magnetically active. On the other hand, when either of the switches SWzp1a and SWzp1b is open, the first shorting winding Zp1 is not grounded and the primary winding P1 is magnetically active to couple with the first secondary winding S1 and or the second secondary winding S2 for transmitting a pulse signal to a transducer element. Thus, by not grounding the first shorting winding Zp1, the primary winding P1 functionally switches the front-end circuit into the TX mode. In contrast, when both of the switches SWzp1a and SWzp1b are closed, the ultrasound front-end circuit is in the RX mode since no pulse signal is outputted to either of the secondary windings S1/S2 since the primary winding P1 is not magnetically active.

During the TX mode, by turning on and off the switches SWp1a and SWp1b, a pulsed signal or waveform is generated at the primary winding P1 according to a transmitter signal from the transmitter 10 and is outputted through the primary winding P1 to one of the secondary windings S1 and S2 that are selectively coupled to the primary winding P1. Also during the TX mode, the secondary shorting windings ZS1 and ZS2 are used to determine which of Zprobe1 or Zprobe2 impedance is connected via the selected one of the secondary windings S1 and S2 so as to receive the pulsed waveform. That is, either one of the secondary shorting windings ZS1 and ZS2 is alternately grounded by closing only one corresponding pair of the switches SWz2a/SWz2b and the switches SWz1a/SWz1b according to the transmitter signal from the transmitter 10. Consequently, the pulsed signal from the primary winding P1 is outputted to Zprobe1 or Zprobe2 at a time via a selected one of the secondary windings S1 and S2 whose associated secondary shorting winding ZS1 or ZS2 is not grounded.

During the receive (RX) mode, the receiver 20 is selectively connected to the selected one of two output nodes via the multiplexer 60 from the secondary windings S1 and S2. To receive one echo signal from a transducer element via either one of the secondary windings S1 and S2, a corresponding one of the two pairs of the switches SWz1a/SWz1b and SWz2a/SWz2b is closed depending on which probe impedance was selected during the TX mode. That is, by shorting the secondary shorting winding ZS1 or ZS2, the associated grounded secondary winding provides a low impedance path for the echo signal to travel as an input to the receiver 20. At the same time, the other one of the two pairs of the switches SWz1a/SWz1b and SWz2a/SWz2b is optionally kept open. An echo signal from the other one of the secondary windings S1 and S2 does not interfere with the input to the receiver 20 since the multiplexer 60 selects an echo signal from the Zprobe1 or the Zprobe2 at a time along with the impedance components Z31 and Z32. Impedance components Z31 and Z32 are used to short one side of winding so that a voltage develops across one of the selected secondary windings S1 and S2. The impedance components Z31 and Z32 are also used to protect the input of the receiver 20 along with the multiplexer 60.

Figure 4C:
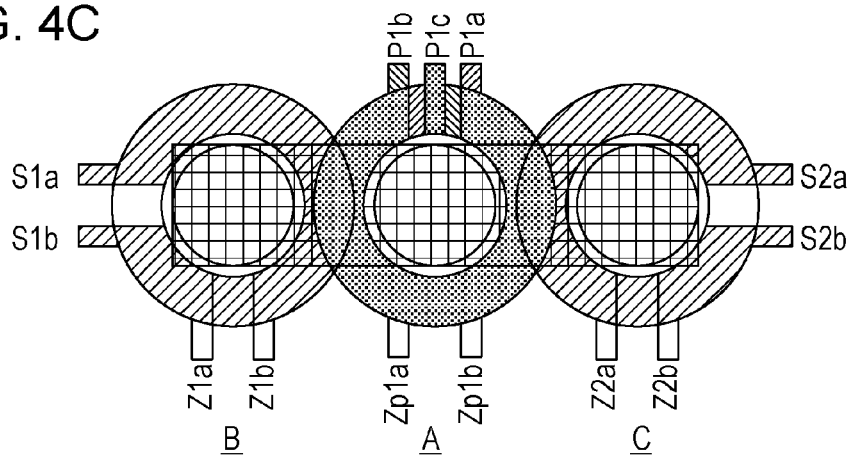
FIG. 4C is a diagram illustrating a cross sectional view of the core of the transformer-based multiplexer in the third embodiment of the current invention.

Now referring to FIG. 4C, a diagram illustrates a cross sectional view of the core of the transformer-based multiplexer in one embodiment of the current invention. On the pole A, the primary winding P1 and the first shorting winding Zp1 are placed at a predetermined ratio. The primary winding P1 has its endings P1a and P1b as well as its tapping point P1c while the first shorting winding Zp1 has its endings Zp1a and Zp1b. By the same token, on the pole B, the first secondary winding S1 and the first secondary shorting winding Zs1 are placed at a predetermined ratio. The first secondary winding S1 has its endings S1a and S1b while the first secondary shorting winding Zs1 has its endings Z1a and Z1b. On the pole C, the second secondary winding S2 and the second secondary shorting winding Zs2 are placed at a predetermined ratio. The second secondary winding S2 has its endings S2a and S2b while the second secondary shorting winding Zs2 has its endings Z2a and Z2b. The pole A is located between the poles B and C so that the secondary windings S1 and S2 are magnetically isolated with each other. On the other hand, the poles B and C are adjacent to the pole A so that the secondary windings S1 and S2 are each magnetically coupled to the primary winding P1. Although the embodiment aligns the poles A, B and C in a straight line, it is not limited to the illustrated configuration.

Figure 5A:
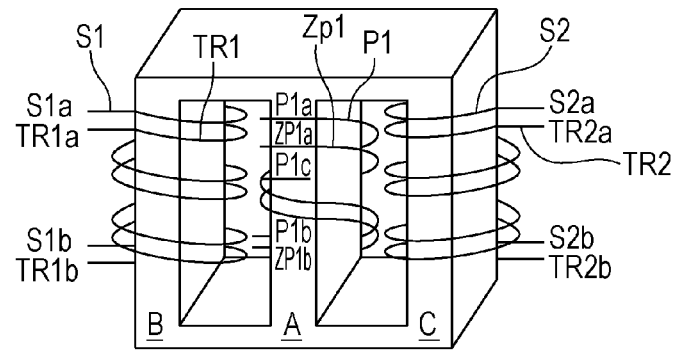
FIG. 5A is a diagram illustrating a transformer core to be used in a fourth embodiment of the multiplexer according to the current invention.

Now referring to FIG. 5A, a diagram illustrating a transformer core to be used in a fourth embodiment of the multiplexer according to the current invention. A primary winding P1 on a first pole A has endings P1a and P1b as well as a tapping terminal P1c. A first shorting winding Zp1 also on the first pole A has endings Zp1a and Zp1b and is magnetically associated with the primary winding P1. A first secondary winding S1 on a second pole B has endings S1a and S1b and is magnetically coupled with the primary winding P1. A first secondary shorting winding TR1 also on the second pole B is magnetically coupled with the first secondary winding S1 and has endings TR1a and TR1b. A second secondary winding S2 on a third pole C has endings S2a and S2b and is magnetically coupled with the primary winding P1. A second secondary shorting winding TR2 also on the third pole C is magnetically coupled with the second secondary winding S2 and has endings TR2a and TR2b. Although the first secondary winding S1 and the second secondary winding S2 are magnetically associated with the primary winding P1, the first secondary winding S1 and the second secondary winding S2 are not magnetically coupled with each other since the poles B and C are provided in a such manner to prevent magnetic coupling. The relative physical locations of the poles A, B and C are merely conceptual and are not limited to the illustrated relation.

Figure 5B:
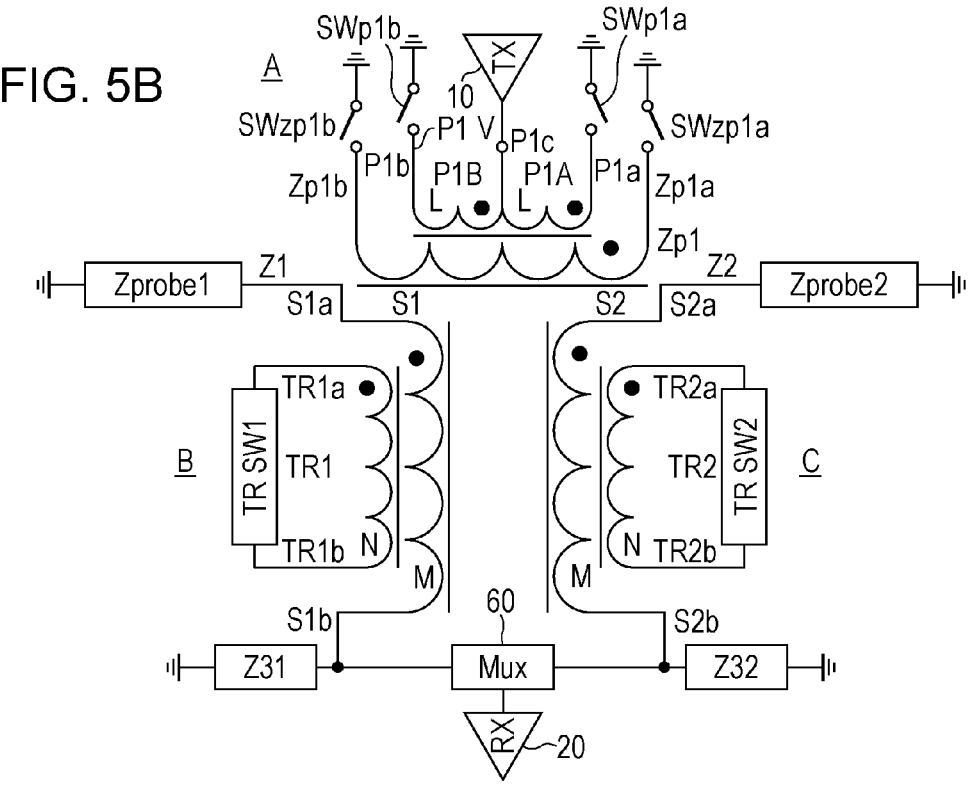
FIG. 5B is a diagram illustrating connections in the transformer-based multiplexer and with the associated components in the fourth embodiment of the ultrasound imaging system according to the current invention.

Now referring to FIG. 5B, a diagram illustrates connections in the transformer-based multiplexer and with the associated components in the fourth embodiment of the ultrasound imaging system according to the current invention. The primary winding P1 and the first shorting winding ZP1 are magnetically coupled on the pole A. The primary winding P1 has two subsections P1A and P1B, and the transmitter TX 10 is tapped in at the terminal P1c between the two subsections P1A and P1B. The primary winding P1 has the terminals P1a and P1b, which are respectively connected to switches SWp1a and SWp1b that are in turn grounded. By turning on and off SWp1a and SWp1b, a pulse is generated according the transmitter signal from the transmitter TX 10. The first shorting winding ZP1 has the terminals Zp1a and Zp1b, which are respectively connected to switches SWzp1a and SWzp1b that are in turn grounded. By closing the switches SWzp1a and SWzp1b, the primary winding P1 is no longer magnetically coupled to other windings as will be later described in detail.

The first secondary winding S1 on the second pole B has the endings S1a and S1b and is magnetically coupled with the primary winding P1. The ending S1a is connected to Zprobe1 such as a transducer element Z1 while the ending S1b is connected to an impedance Z31 and the receiver 20 via a low-voltage multiplexer 60. The first secondary shorting winding TR1 also on the second pole B is magnetically coupled with the first secondary winding S1 and has the endings TR1a and TR1b, which are respectively connected to an active switch TRSW1, which is optionally low voltage. By closing the switch TRSW1, the first secondary winding S1 is no longer magnetically coupled to the primary winding P1 and consequently receives none of the pulsed waveforms from the primary winding P1.

The second secondary winding S2 on the third pole C has the endings S2a and S2b and is magnetically coupled with the primary winding P1. The ending S2a is connected to Zprobe2 such as a transducer element Z2 while the ending S2b is connected to an impedance Z32 and the receiver 20 via the common multiplexer 60. The second secondary shorting winding TR2 also on the third pole C is magnetically coupled with the second secondary winding S2 and has endings TR2a and TR2b, which are respectively connected to an active switch TRSW2, which is optionally low voltage. By closing the switch TRSW2, the second secondary winding S2 is no longer magnetically coupled to the primary winding P1 and consequently receives none of the pulsed waveforms from the primary winding P1.

In the above embodiment of the transformer-based multiplexer, the windings are constructed in a certain manner. Although the first secondary winding S1 and the second secondary winding S2 are magnetically associated with the primary winding P1 in an independent manner, the first secondary winding S1 and the second secondary winding S2 are not magnetically coupled with each other since the poles B and C are provided in a such manner to prevent magnetic coupling. Furthermore, the secondary windings S1 and S2 are electrically isolated from each other for implementing the high-voltage (HV) multiplexer.

In other embodiments of the transformer-based multiplexer, the switches TRSW1 and TRSW2 are either active or passive and include various types such as semiconductors. In addition, the switches TRSW1 and TRSW2 are optionally low-voltage switches and have an advantage of minimal or low loss of power and voltage due its low voltage application.

The above described ultrasound front-end circuit containing the transformer-based multiplexer has two predetermined modes of operation including transmit (TX) and receive (RX). A transmission/receive (TR) switch is implemented using the switches SWzp1a and SWzp1b in combination with the multiplexer 60 and the impedance components Z31 and Z32. When both of the switches SWzp1a and SWzp1b are closed, the first shorting winding Zp1 is grounded and the primary winding P1 is no longer magnetically active. On the other hand, when either of the switches SWzp1a and SWzp1b is open, the first shorting winding Zp1 is not grounded and the primary winding P1 is magnetically active to couple with the first secondary winding S1 and or the second secondary winding S2 for transmitting a pulse signal to a transducer element. Thus, by not grounding the first shorting winding Zp1, the primary winding P1 functionally switches the front-end circuit into the TX mode. In contrast, when both of the switches SWzp1a and SWzp1b are closed, the ultrasound front-end circuit is in the RX mode since no pulse signal is outputted to either of the secondary windings S1/S2 since the primary winding P1 is not magnetically active.

During the TX mode, by turning on and off the switches SWp1a and SWp1b, a pulsed signal or waveform is generated at the primary winding P1 according to a transmitter signal from the transmitter 10 and is outputted through the primary winding P1 to one of the secondary windings S1 and S2 that are selectively coupled to the primary winding P1. Also during the TX mode, the secondary shorting windings TR1 and TR2 are used to determine which of Zprobe1 or Zprobe2 impedance is connected via the selected one of the secondary windings S1 and S2 so as to receive the pulsed waveform. That is, either one of the secondary windings TR1 and TR2 is alternately grounded by closing only one the switches TRSW1 and TRSW2 according to the transmitter signal from the transmitter 10. Consequently, the pulsed signal from the primary winding P1 is outputted to Zprobe1 or Zprobe2 at a time via a selected one of the secondary windings S1 and S2 whose associated secondary shorting winding TR1 or TR2 is not grounded.

During the receive (RX) mode, the receiver 20 is selectively connected to the selected one of two output nodes via the multiplexer 60 from the secondary windings S1 and S2. To receive one echo signal from a transducer element via either one of the secondary windings S1 and S2, a corresponding one of the two switches TRSW1 and TRSW2 is closed depending on which probe impedance was selected during the TX mode. That is, by shorting the secondary winding TR1 or TR2, the associated grounded secondary winding provides a low impedance path for the echo signal to travel as an input to the receiver 20. At the same time, the other one of the two switches TRSW1 and TRSW2 is optionally kept open. An echo signal from the other one of the secondary windings S1 and S2 does not interfere with the input to the receiver 20 since the multiplexer 60 selects an echo signal from the Zprobe1 or the Zprobe2 at a time along with the impedance components Z31 and Z32. Impedance components Z31 and Z32 are used to short one side of winding so that a voltage develops across one of the selected secondary windings S1 and S2. The impedance components Z31 and Z32 are also used to protect the input of the receiver 20 along with the multiplexer 60.

Figure 5C:
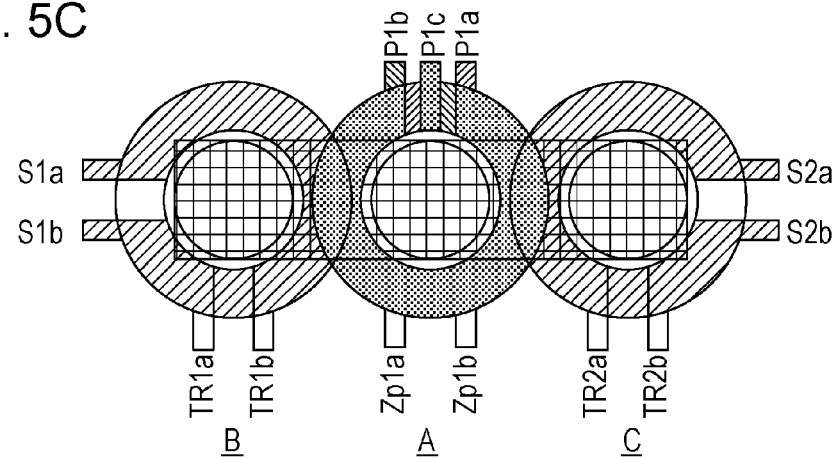
FIG. 5C is a diagram illustrating a cross sectional view of the core of the transformer-based multiplexer in the fourth embodiment of the current invention.

Now referring to FIG. 5C, a diagram illustrates a cross sectional view of the core of the transformer-based multiplexer in one embodiment of the current invention. On the pole A, the primary winding P1 and the first shorting winding Zp1 are placed at a predetermined ratio. The primary winding P1 has its endings P1a and P1b as well as its tapping point P1c while the first shorting winding Zp1 has its endings Zp1a and Zp1b. By the same token, on the pole B, the first secondary winding S1 and the first secondary shorting winding TR1 are placed at a predetermined ratio. The first secondary winding S1 has its endings S1a and S1b while the first secondary shorting winding TR1 has its endings TR1a and TR1b. On the pole C, the second secondary winding S2 and the second secondary shorting winding TR2 are placed at a predetermined ratio. The second secondary winding S2 has its endings S2a and S2b while the second secondary shorting winding TR2 has its endings TR2a and TR2b. The pole A is located between the poles B and C so that the secondary windings S1 and S2 are magnetically isolated with each other. On the other hand, the poles B and C are adjacent to the pole A so that the secondary windings S1 and S2 are each magnetically coupled to the primary winding P1. Although the embodiment aligns the poles A, B and C in a straight line, it is not limited to the illustrated configuration.

Figure 6A:
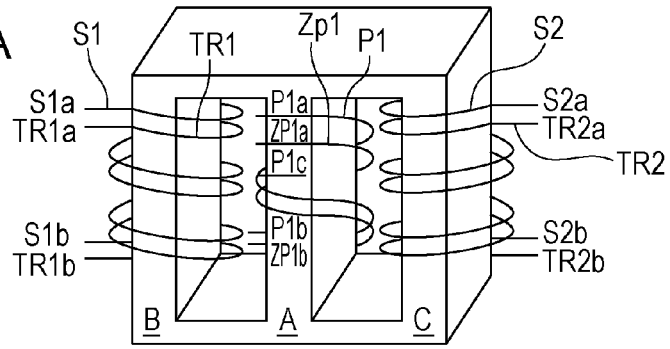
FIG. 6A is a diagram illustrating a transformer core to be used in a fifth embodiment of the multiplexer according to the current invention.

Now referring to FIG. 6A, a diagram illustrating a transformer core to be used in a fifth embodiment of the multiplexer according to the current invention. A primary winding P1 on a first pole A has endings P1a and P1b as well as a tapping terminal P1c. A first shorting winding Zp1 also on the first pole A has endings Zp1a and Zp1b and is magnetically associated with the primary winding P1. A first secondary winding S1 on a second pole B has endings S1a and S1b and is magnetically coupled with the primary winding P1. A first secondary shorting winding TR1 also on the second pole B is magnetically coupled with the first secondary winding S1 and has endings TR1a and TR1b. A second secondary winding S2 on a third pole C has endings S2a and S2b and is magnetically coupled with the primary winding P1. A second secondary shorting winding TR2 also on the third pole C is magnetically coupled with the second secondary winding S2 and has endings TR2a and TR2b. Although the first secondary winding S1 and the second secondary winding S2 are magnetically associated with the primary winding P1, the first secondary winding S1 and the second secondary winding S2 are not magnetically coupled with each other since the poles B and C are provided in a such manner to prevent magnetic coupling. The relative physical locations of the poles A, B and C are merely conceptual and are not limited to the illustrated relation.

Figure 6B:
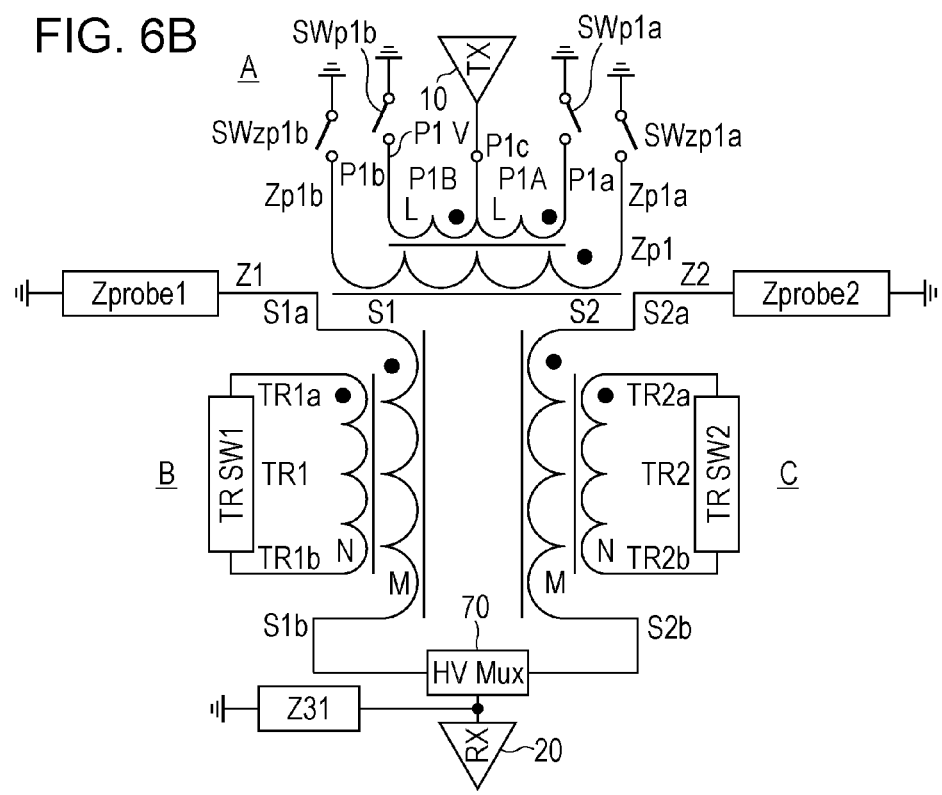
FIG. 6B is a diagram illustrating connections in the transformer-based multiplexer and with the associated components in the fifth embodiment of the ultrasound imaging system according to the current invention.

Now referring to FIG. 6B, a diagram illustrates connections in the transformer-based multiplexer and with the associated components in the fifth embodiment of the ultrasound imaging system according to the current invention. The primary winding P1 and the first shorting winding ZP1 are magnetically coupled on the pole A. The primary winding P1 has two subsections P1A and P1B, and the transmitter TX 10 is tapped in at the terminal P1c between the two subsections P1A and P1B. The primary winding P1 has the terminals P1a and P1b, which are respectively connected to switches SWp1a and SWp1b that are in turn grounded. By turning on and off SWp1a and SWp1b, a pulse is generated according the transmitter signal from the transmitter TX 10. The first shorting winding ZP1 has the terminals Zp1a and Zp1b, which are respectively connected to switches SWzp1a and SWzp1b that are in turn grounded. By closing the switches SWzp1a and SWzp1b, the primary winding P1 is no longer magnetically coupled to other windings as will be later described in detail.

The first secondary winding S1 on the second pole B has the endings S1a and S1b and is magnetically coupled with the primary winding P1. The ending S1a is connected to Zprobe1 such as a transducer element Z1 while the ending S1b is connected to an impedance Z31 via a high-voltage multiplexer 70 and the receiver 20 via the high-voltage multiplexer 70. The first secondary shorting winding TR1 also on the second pole B is magnetically coupled with the first secondary winding S1 and has the endings TR1a and TR1b, which are respectively connected to an active switch TRSW1, which is optionally low voltage. By closing the switch TRSW1, the first secondary winding S1 is no longer magnetically coupled to the primary winding P1 and consequently receives none of the pulsed waveforms from the primary winding P1.

The second secondary winding S2 on the third pole C has the endings S2a and S2b and is magnetically coupled with the primary winding P1. The ending S2a is connected to Zprobe2 such as a transducer element Z2 while the ending S2b is connected to the impedance Z31 and the receiver 20 both via the common multiplexer 70. The second secondary shorting winding TR2 also on the third pole C is magnetically coupled with the second secondary winding S2 and has endings TR2a and TR2b, which are respectively connected to an active switch TRSW2, which is optionally low voltage. By closing the switch TRSW2, the second secondary winding S2 is no longer magnetically coupled to the primary winding P1 and consequently receives none of the pulsed waveforms from the primary winding P1.

In the above embodiment of the transformer-based multiplexer, the windings are constructed in a certain manner. Although the first secondary winding S1 and the second secondary winding S2 are magnetically associated with the primary winding P1 in an independent manner, the first secondary winding S1 and the second secondary winding S2 are not magnetically coupled with each other since the poles B and C are provided in a such manner to prevent magnetic coupling. Furthermore, the secondary windings S1 and S2 are electrically isolated from each other for implementing the high-voltage (HV) multiplexer.

In other embodiments of the transformer-based multiplexer, the switches TRSW1 and TRSW2 are either active or passive and include various types such as semiconductors. In addition, the switches TRSW1 and TRSW2 are optionally low-voltage switches and have an advantage of minimal or low loss of power and voltage due its low voltage application.

The above described ultrasound front-end circuit containing the transformer-based multiplexer has two predetermined modes of operation including transmit (TX) and receive (RX). A transmission/receive (TR) switch is implemented using the switches SWzp1a and SWzp1b in combination with the multiplexer 70 and the impedance component Z31. When both of the switches SWzp1a and SWzp1b are closed, the first shorting winding Zp1 is grounded and the primary winding P1 is no longer magnetically active. On the other hand, when either of the switches SWzp1a and SWzp1b is open, the first shorting winding Zp1 is not grounded and the primary winding P1 is magnetically active to couple with the first secondary winding S1 and or the second secondary winding S2 for transmitting a pulse signal to a transducer element. Thus, by not grounding the first shorting winding Zp1, the primary winding P1 functionally switches the front-end circuit into the TX mode. In contrast, when both of the switches SWzp1a and SWzp1b are closed, the ultrasound front-end circuit is in the RX mode since no pulse signal is outputted to either of the secondary windings S1/S2 since the primary winding P1 is not magnetically active.

During the TX mode, by turning on and off the switches SWp1a and SWp1b, a pulsed signal or waveform is generated at the primary winding P1 according to a transmitter signal from the transmitter 10 and is outputted through the primary winding P1 to one of the secondary windings S1 and S2 that are selectively coupled to the primary winding P1. Also during the TX mode, the secondary shorting windings TR1 and TR2 are used to determine which of Zprobe1 or Zprobe2 impedance is connected via the selected one of the secondary windings S1 and S2 so as to receive the pulsed waveform. That is, either one of the secondary windings TR1 and TR2 is alternately grounded by closing only one the switches TRSW1 and TRSW2 according to the transmitter signal from the transmitter 10. Consequently, the pulsed signal from the primary winding P1 is outputted to Zprobe1 or Zprobe2 at a time via a selected one of the secondary windings S1 and S2 whose associated secondary shorting winding TR1 or TR2 is not grounded.

During the receive (RX) mode, the receiver 20 is selectively connected to the selected one of two output nodes via the multiplexer 70 from the secondary windings S1 and S2. To receive one echo signal from a transducer element via either one of the secondary windings S1 and S2, a corresponding one of the two switches TRSW1 and TRSW2 is closed depending on which probe impedance was selected during the TX mode. That is, by shorting the secondary winding TR1 or TR2, the associated grounded secondary winding provides a low impedance path for the echo signal to travel as an input to the receiver 20. At the same time, the other one of the two switches TRSW1 and TRSW2 is optionally kept open. An echo signal from the other one of the secondary windings S1 and S2 does not interfere with the input to the receiver 20 since the multiplexer 70 selects an echo signal from the Zprobe1 or the Zprobe2 at a time. Impedance component Z31 is used to short one side of winding so that a voltage develops across one of the selected secondary windings S1 and S2. The impedance component Z31 is also used to protect the input of the receiver 20 along with the multiplexer 70.

Figure 6C:
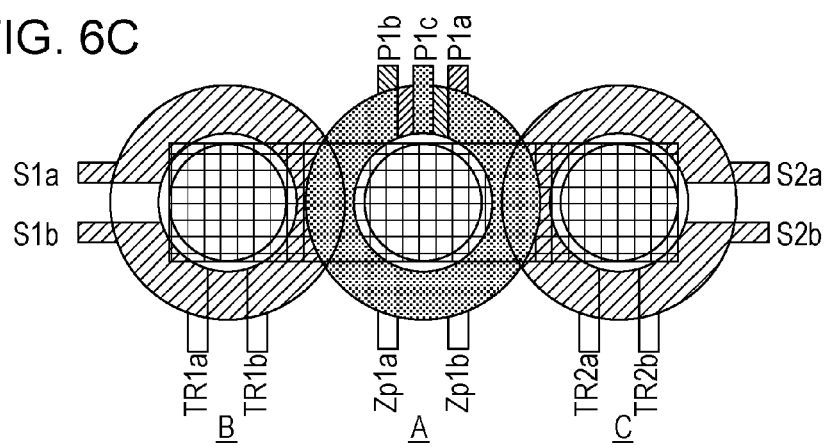
FIG. 6C is a diagram illustrating a cross sectional view of the core of the transformer-based multiplexer in the fifth embodiment of the current invention.

Now referring to FIG. 6C, a diagram illustrates a cross sectional view of the core of the transformer-based multiplexer in one embodiment of the current invention. On the pole A, the primary winding P1 and the first shorting winding Zp1 are placed at a predetermined ratio. The primary winding P1 has its endings P1a and P1b as well as its tapping point P1c while the first shorting winding Zp1 has its endings Zp1a and Zp1b. By the same token, on the pole B, the first secondary winding S1 and the first secondary shorting winding TR1 are placed at a predetermined ratio. The first secondary winding S1 has its endings S1a and S1b while the first secondary shorting winding TR1 has its endings TR1a and TR1b. On the pole C, the second secondary winding S2 and the second secondary shorting winding TR2 are placed at a predetermined ratio. The second secondary winding S2 has its endings S2a and S2b while the second secondary shorting winding TR2 has its endings TR2a and TR2b. The pole A is located between the poles B and C so that the secondary windings S1 and S2 are magnetically isolated with each other. On the other hand, the poles B and C are adjacent to the pole A so that the secondary windings S1 and S2 are each magnetically coupled to the primary winding P1. Although the embodiment aligns the poles A, B and C in a straight line, it is not limited to the illustrated configuration.

Figure 7A:
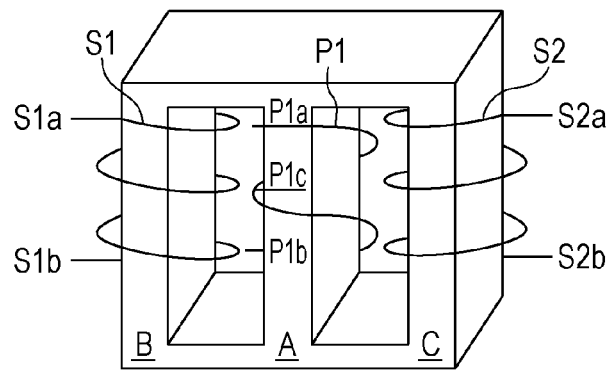
FIG. 7A is a diagram illustrating a transformer core to be used in a sixth embodiment of the multiplexer according to the current invention.

Now referring to FIG. 7A, a diagram illustrating a transformer core to be used in a sixth embodiment of the multiplexer according to the current invention. A primary winding P1 on a first pole A has endings P1a and P1b as well as a tapping terminal P1c. A first secondary winding S1 on a second pole B has endings S1a and S1b and is magnetically coupled with the primary winding P1. A second secondary winding S2 on a third pole C has endings S2a and S2b and is magnetically coupled with the primary winding P1. Although the first secondary winding S1 and the second secondary winding S2 are magnetically associated with the primary winding P1, the first secondary winding S1 and the second secondary winding S2 are not magnetically coupled with each other since the poles B and C are provided in a such manner to prevent magnetic coupling. The relative physical locations of the poles A, B and C are merely conceptual and are not limited to the illustrated relation.

Figure 7B:
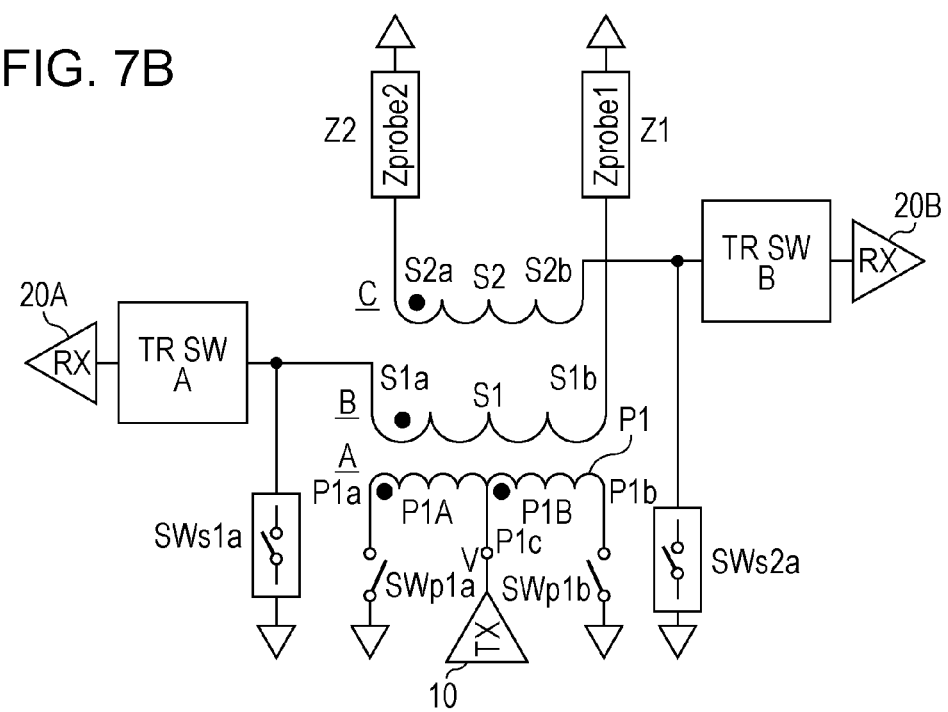
FIG. 7B is a diagram illustrating connections in the transformer-based multiplexer and with the associated components in the sixth embodiment of the ultrasound imaging system according to the current invention.

Now referring to FIG. 7B, a diagram illustrates connections in the transformer-based multiplexer and with the associated components in the sixth embodiment of the ultrasound imaging system according to the current invention. The primary winding P1 on the pole A has two subsections P1A and P1B, and the transmitter TX 10 is tapped in at the terminal P1C between the two subsections P1A and P1B. The primary winding P1 has the terminals P1a and P1b, which are respectively connected to switches SWp1a and SWp1b that are in turn grounded. By turning on and off SWp1a and SWp1b, a pulse is generated according the transmitter signal from the transmitter TX 10.

The first secondary winding S1 on the second pole B has the endings S1a and S1b and is magnetically coupled with the primary winding P1. The ending S1b is connected to Zprobe1 such as a transducer element Z1 while the ending S1a is connected to a first secondary winding switch SWs1a that in turn is grounded and a first receiver RX 20A via a first transmit/receive switch TRSW A. By closing the first secondary winding switch SWs1a during the transmit mode as operationally controlled by the first transmit/receive switch TRSW A, the first secondary winding S1 no longer sends the pulsed waveforms from the primary winding P1 to the transducer element Z1 since the first secondary winding S1 is grounded at one end.

The second secondary winding S2 on the second pole C has the endings S2a and S2b and is magnetically coupled with the primary winding P1. The ending S2a is connected to Zprobe2 such as a transducer element Z2 while the ending S2b is connected to a second secondary winding switch SWs2a that in turn is grounded and a second receiver RX 20B via a second transmit/receive switch TRSW B. By closing the first secondary winding switch SWs2a during the transmit mode as operationally controlled by the second transmit/receive switch TRSW B, the second secondary winding S2 no longer sends the pulsed waveforms from the primary winding P1 to the transducer element Z2 since the second secondary winding S2 is grounded at one end.

In the above embodiment of the transformer-based multiplexer, the windings are constructed in a certain manner. Although the first secondary winding S1 and the second secondary winding S2 are magnetically associated with the primary winding P1 in an independent manner, the first secondary winding S1 and the second secondary winding S2 are not magnetically coupled with each other since the poles B and C are provided in a such manner to prevent magnetic coupling. Furthermore, the secondary windings S1 and S2 are electrically isolated from each other for implementing the high-voltage (HV) multiplexer.

The above described ultrasound front-end circuit containing the transformer-based multiplexer has two predetermined modes of operation including transmit (TX) and receive (RX) using the transmission/receive (TR) switches TRSW A and TRSW B. When the switches SWp1a and SWp1b are closed, the primary winding P1 is no longer magnetically active. On the other hand, when either of the switches SWp1a and SWp1b is open, the primary winding P1 is magnetically active to couple with the first secondary winding S1 and or the second secondary winding S2 for transmitting a pulse signal to a transducer element. Thus, by not grounding the primary winding P1, the primary winding P1 functionally switches the front-end circuit into the TX mode. In contrast, when both of the switches SWp1a and SWp1b are closed, the ultrasound front-end circuit is in the RX mode since no pulse signal is outputted to either of the secondary windings S1/S2 since the primary winding P1 is not magnetically active.

During the TX mode, by turning on and off the switches SWp1a and SWp1b, a pulsed signal or waveform is generated at the primary winding P1 according to a transmitter signal from the transmitter TX 10 and is outputted through the primary winding P1 to one of the secondary windings S1 and S2 that are selectively coupled to the primary winding P1. During the TX mode, the TR switches TRSW A and TRSW B are used to prevent the receivers 20A and 20B from receiving any input. Also during the TX mode, the first secondary winding switch SWs1a and the second secondary winding switch SWs2a are used to determine which of Zprobe1 or Zprobe2 impedance is connected via the selected one of the secondary windings S1 and S2 so as to receive the pulsed waveform. That is, either one of the secondary windings S1 and S2 is alternately grounded by closing one of the secondary winding switches SWs1a and SWs2a according to the transmitter signal from the transmitter TX 10. Consequently, the pulsed signal from the primary winding P1 is outputted to Zprobe1 or Zprobe2 at a time via a selected one of the secondary windings S1 and S2 whose associated secondary switches SWs1a and SWs2a is not grounded.

During the receive (RX) mode, either one of the receivers RX 20A and 20B is selectively connected to the two independent output nodes via the secondary winding S1 or S2. During the RX mode, the TR switches TRSW A and TRSW B are used to connect the receivers 20A and 20B for receiving an input. To receive one echo signal from a transducer element via either one of the secondary windings S1 and S2, a corresponding one of the secondary switches SWs1a and SWs2a is opened depending on which probe impedance was selected during the TX mode. That is, by opening the secondary switches SWs1a and SWs2a, the associated secondary winding has a low impedance path for the echo signal to travel as an input to the receiver 20A or 20B via the TR switches TRSW A and TRSW B. At the same time, the other one of the two switches SWs1a and SWs2a is optionally kept closed. Since the path to the receiver 20A or 20B is independent, an echo signal from the other one of the secondary windings S1 and S2 does not interfere with the input to the receivers 20A or 20B.

Figure 7C:
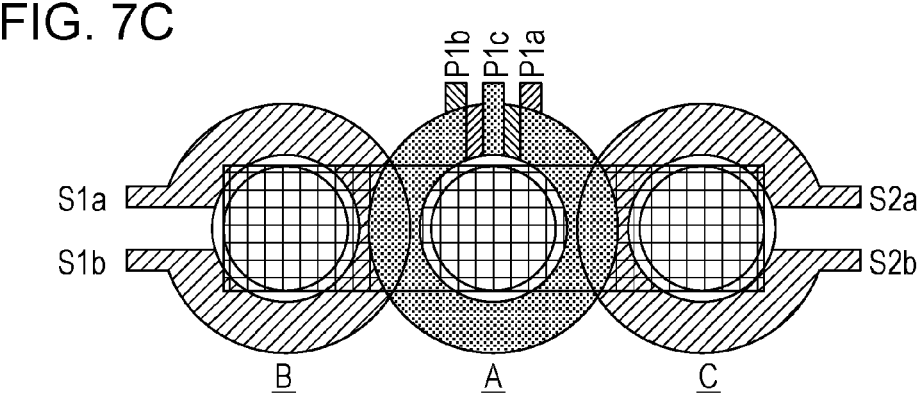
FIG. 7C is a diagram illustrating a cross sectional view of the core of the transformer-based multiplexer in the sixth embodiment of the current invention.

Now referring to FIG. 7C, a diagram illustrates a cross sectional view of the core of the transformer-based multiplexer in one embodiment of the current invention. On the pole A, the primary winding P1 is placed and has its endings P1a and P1b as well as its tapping point P1c. By the same token, on the pole B, the first secondary winding S1 is placed and has its endings S1a and S1b. On the pole C, the second secondary winding S2 is placed and has its endings S2a and S2b. The pole A is located between the poles B and C so that the secondary windings S1 and S2 are magnetically isolated with each other. On the other hand, the poles B and C are adjacent to the pole A so that the secondary windings S1 and S2 are each magnetically coupled to the primary winding P1. Although the embodiment aligns the poles A, B and C in a straight line, it is not limited to the illustrated configuration.

Figure 8A:
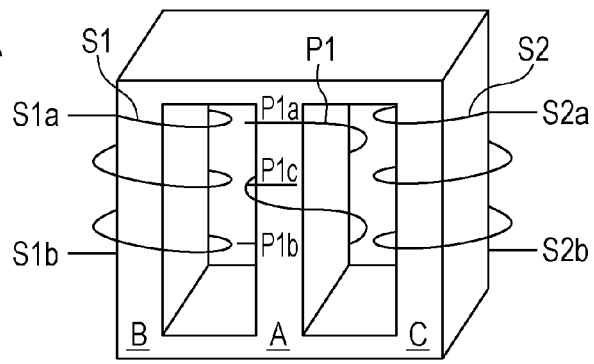
FIG. 8A is a diagram illustrating a transformer core to be used in a seventh embodiment of the multiplexer according to the current invention.

Now referring to FIG. 8A, a diagram illustrating a transformer core to be used in a seventh embodiment of the multiplexer according to the current invention. A primary winding P1 on a first pole A has endings P1a and P1b as well as a tapping terminal P1c. A first secondary winding S1 on a second pole B has endings S1a and S1b and is magnetically coupled with the primary winding P1. A second secondary winding S2 on a third pole C has endings S2a and S2b and is magnetically coupled with the primary winding P1. Although the first secondary winding S1 and the second secondary winding S2 are magnetically associated with the primary winding P1, the first secondary winding S1 and the second secondary winding S2 are not magnetically coupled with each other since the poles B and C are provided in a such manner to prevent magnetic coupling. The relative physical locations of the poles A, B and C are merely conceptual and are not limited to the illustrated relation.

Figure 8B:
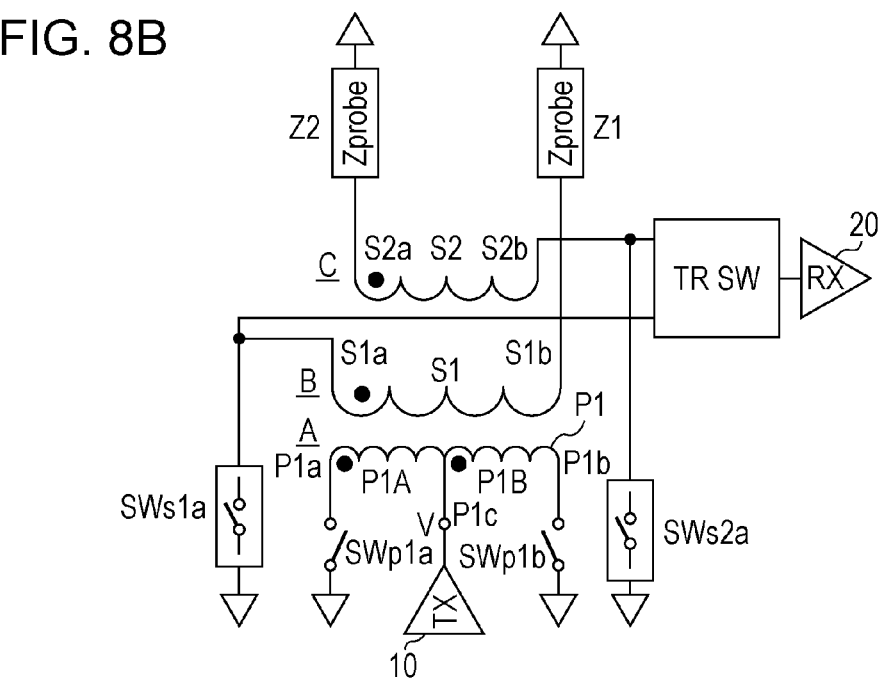
FIG. 8B is a diagram illustrating connections in the transformer-based multiplexer and with the associated components in the seventh embodiment of the ultrasound imaging system according to the current invention.

Now referring to FIG. 8B, a diagram illustrates connections in the transformer-based multiplexer and with the associated components in the seventh embodiment of the ultrasound imaging system according to the current invention. The primary winding P1 on the pole A has two subsections P1A and P1B, and the transmitter TX 10 is tapped in at the terminal P1C between the two subsections P1A and P1B. The primary winding P1 has the terminals P1a and P1b, which are respectively connected to switches SWp1a and SWp1b that are in turn grounded. By turning on and off SWp1a and SWp1b, a pulse is generated according the transmitter signal from the transmitter TX 10.

The first secondary winding S1 on the second pole B has the endings S1a and S1b and is magnetically coupled with the primary winding P1. The ending S1b is connected to Zprobe1 such as a transducer element Z1 while the ending S1a is connected to a first secondary winding switch SWs1a that in turn is grounded and a receiver RX 20 via a transmit/receive switch TRSW. By closing the first secondary winding switch SWs1a during the transmit mode as operationally controlled by the transmit/receive switch TRSW, the first secondary winding S1 no longer sends the pulsed waveforms from the primary winding P1 to the transducer element Z1 since the first secondary winding S1 is grounded at one end.

The second secondary winding S2 on the second pole C has the endings S2a and S2b and is magnetically coupled with the primary winding P1. The ending S2a is connected to Zprobe2 such as a transducer element Z2 while the ending S2b is connected to a second secondary winding switch SWs2a that in turn is grounded and the receiver RX 20 via the transmit/receive switch TRSW. By closing the second secondary winding switch SWs2a during the transmit mode as operationally controlled by the transmit/receive switch TRSW, the second secondary winding S2 no longer sends the pulsed waveforms from the primary winding P1 to the transducer element Z2 since the second secondary winding S2 is grounded at one end.

In the above embodiment of the transformer-based multiplexer, the windings are constructed in a certain manner. Although the first secondary winding S1 and the second secondary winding S2 are magnetically associated with the primary winding P1 in an independent manner, the first secondary winding S1 and the second secondary winding S2 are not magnetically coupled with each other since the poles B and C are provided in a such manner to prevent magnetic coupling. Furthermore, the secondary windings S1 and S2 are electrically isolated from each other for implementing the high-voltage (HV) multiplexer.

The above described ultrasound front-end circuit containing the transformer-based multiplexer has two predetermined modes of operation including transmit (TX) and receive (RX) using the switches SWp1a and SWp1b and the transmission/receive (TR) switch TRSW. When the switches SWp1a and SWp1b are closed, the primary winding P1 is no longer magnetically active. On the other hand, when either of the switches SWp1a and SWp1b is open, the primary winding P1 is magnetically active to couple with the secondary winding S1 and or S2 for transmitting a pulse signal to a transducer element. Thus, by not grounding the primary winding P1, the primary winding P1 functionally switches the front-end circuit into the TX mode. In contrast, when both of the switches SWp1a and SWp1b are closed, the ultrasound front-end circuit is in the RX mode since no pulse signal is outputted to either of the secondary windings S1 and S2 since the primary winding P1 is not magnetically active.

During the TX mode, by turning on and off the switches SWp1a and SWp1b, a pulsed signal or waveform is generated at the primary winding P1 according to a transmitter signal from the transmitter TX 10 and is outputted through the primary winding P1 to one of the secondary windings S1 and S2 that are selectively coupled to the primary winding P1. During the TX mode, the TR switch TRSW is used to prevent the receiver 20 from receiving any input. Also during the TX mode, the first secondary winding switch SWs1a and the second secondary winding switch SWs2a are used to determine which of Zprobe1 or Zprobe2 impedance is connected via the selected one of the secondary windings S1 and S2 so as to receive the pulsed waveform. That is, either one of the secondary windings S1 and S2 is alternately grounded by closing one of the secondary winding switches SWs1a and SWs2a according to the transmitter signal from the transmitter TX 10. Consequently, the pulsed signal from the primary winding P1 is outputted to Zprobe1 or Zprobe2 at a time via a selected one of the secondary windings S1 and S2 whose associated secondary switches SWs1a and SWs2a is not grounded.

During the receive (RX) mode, the receiver RX 20 is connected to the two independent output nodes via the secondary winding S1 or S2. During the RX mode, the TR switch TRSW is used to connect the receiver 20 for receiving an input. To receive one echo signal from a transducer element via either one of the secondary windings S1 and S2, a corresponding one of the secondary switches SWs1a and SWs2a is opened depending on which probe impedance was selected during the TX mode. That is, by opening the secondary switches SWs1a and SWs2a, the associated secondary winding has a low impedance path for the echo signal to travel as an input to the receiver 20 via the TR switch TRSW. At the same time, the other one of the two switches SWs1a and SWs2a is optionally kept closed. Since the path to the receiver 20 is independent, an echo signal from the other one of the secondary windings S1 and S2 does not interfere with the input to the receiver 20.

Figure 8C:
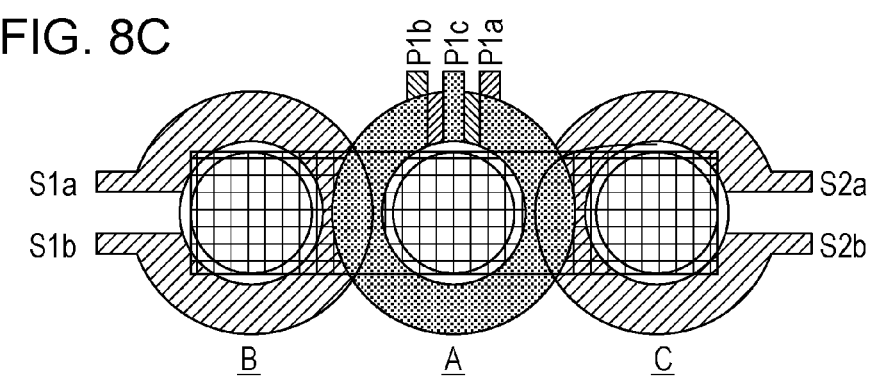
FIG. 8C is a diagram illustrating a cross sectional view of the core of the transformer-based multiplexer in the seventh embodiment of the current invention.

Now referring to FIG. 8C, a diagram illustrates a cross sectional view of the core of the transformer-based multiplexer in one embodiment of the current invention. On the pole A, the primary winding P1 is placed and has its endings P1a and P1b as well as its tapping point P1c. By the same token, on the pole B, the first secondary winding S1 is placed and has its endings S1a and S1b. On the pole C, the second secondary winding S2 is placed and has its endings S2a and S2b. The pole A is located between the poles B and C so that the secondary windings S1 and S2 are magnetically isolated with each other. On the other hand, the poles B and C are adjacent to the pole A so that the secondary windings S1 and S2 are each magnetically coupled to the primary winding P1. Although the embodiment aligns the poles A, B and C in a straight line, it is not limited to the illustrated configuration.

Figure 9A:
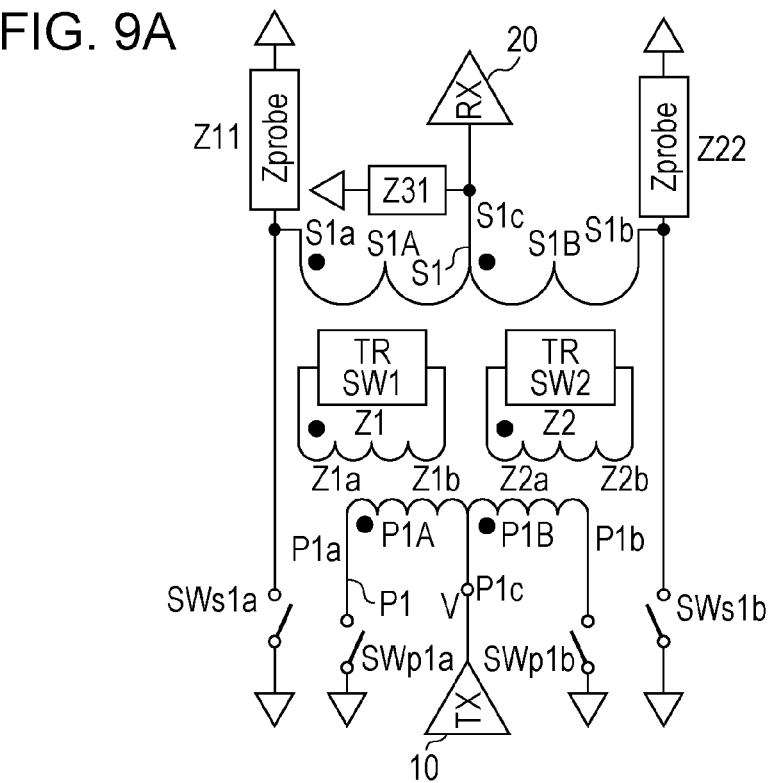
FIG. 9A is a diagram illustrating a transformer core to be used in an eighth embodiment of the multiplexer according to the current invention.

Now referring to FIG. 9A, a diagram illustrates connections in the transformer-based multiplexer and with the associated components in the eighth embodiment of the ultrasound imaging system according to the current invention. The primary winding P1 has two subsections P1A and P1B, and the transmitter TX 10 is tapped in at the terminal P1C between the two subsections P1A and P1B. The primary winding P1 has the terminals P1a and P1b, which are respectively connected to switches SWp1a and SWp1b that are in turn grounded. By turning on and off SWp1a and SWp1b, a pulse is generated according the transmitter signal from the transmitter TX 10.

Two shorting windings Z1 and Z2 are magnetically coupled to the corresponding sub-divided primary windings P1A and P1B in a separate manner. The first shorting winding Z1 has endings Z1a and Z1b, which are connected to a transmission/receive (TR) switch TRSW1. Similarly, the second shorting winding Z2 has endings Z2a and Z2b, which are connected to a transmission/receive (TR) switch TRSW2. The shorting windings Z1 and Z2 are respectively controlled by TR switches TRSW1 and TRSW2 to independently ground the primary winding portions P1A and P1B.

A secondary winding S1 also has two sub-divided winding portions S1A and S1B, which are magnetically coupled with the primary winding portions P1A and P1B in a corresponding manner. That is, the secondary winding portion S1A is magnetically coupled with the primary winding portion P1A while the secondary winding portion S1B is magnetically coupled with the primary winding portion P1B.

Furthermore, the secondary winding S1 has a tapping terminal S1c for a receiver RX 20 as well as the endings S1a and S1b that are connected to the probe transducer elements. The ending S1a is connected to Zprobe1 such as a transducer element Z11 and a secondary winding first switch SWs1a that in turn is grounded. The ending S1b is connected to Zprobe2 such as a transducer element Z22 and a secondary winding second switch SWs1b that in turn is grounded. In addition, the secondary winding S1 is tapped by the receiver RX 20 and an impedance component Z31 at the predetermined terminal S1c on the secondary winding S1.

In the above embodiment of the transformer-based multiplexer, the windings are constructed in a certain manner. Although the first and second portions P1A and P1B of the primary winding P1 are magnetically associated with the secondary winding S1, the first and second portions P1A and P1B are not magnetically coupled with each other. By the same token, although the first and second portions S1A and S1B of the secondary winding S1 are magnetically associated with the primary winding P1 in an independent manner, the first and second portions S1A and S1B are not magnetically coupled with each other. Furthermore, the first and second portions P1A and P1B of the primary winding P1 and the first and second portions S1A and S1B of the secondary winding S1 are electrically isolated from each other for implementing the high-voltage (HV) multiplexer. Similarly, the first shorting winding Z1 and the second shorting winding Z2 are also electrically isolated from each other for implementing the high-voltage (HV) multiplexer.

The above described ultrasound front-end circuit containing the transformer-based multiplexer has two predetermined modes of operation including transmit (TX) and receive (RX) using the switches SWp1a and SWp1b and the transmission/receive (TR) switches TRSW1 and TRSW2. When the switches SWp1a and SWp1b are closed, the primary winding P1 is no longer magnetically active. On the other hand, when either of the switches SWp1a and SWp1b is open, the primary winding P1 is magnetically active to couple with the first secondary winding S1 for transmitting a pulse signal to a transducer element. Thus, by not grounding the primary winding P1, the primary winding P1 functionally switches the front-end circuit into the TX mode. In contrast, when both of the switches SWp1a and SWp1b are closed, the ultrasound front-end circuit is in the RX mode since no pulse signal is outputted to either of the secondary winding S1 since the primary winding P1 is not magnetically active.

During the TX mode, by turning on and off the switches SWp1a and SWp1b, a pulsed signal or waveform is generated at the primary winding P1 according to a transmitter signal from the transmitter TX 10 and is outputted through the primary winding P1 to one of the secondary winding portions S1A and or S1B that are selectively coupled to the corresponding portions P1A and P1B of the primary winding P1. During the TX mode, the impedance Z31 is used to prevent the receiver 20 from receiving any input. Also during the TX mode, the TR switches TRSW1 and TRSW2 are used to determine which of Zprobe1 or Zprobe2 impedance is connected via the selected one of the primary winding portions P1A and P1B. Furthermore, either one of the secondary winding portions S1A and S1B is alternately grounded by closing one of the secondary winding switches SWs1a and SWs2a according to the transmitter signal from the transmitter TX 10. Consequently, the pulsed signal from the primary winding portion P1A or P1B is outputted to Zprobe1 or Zprobe2 at a time via a selected one of the secondary winding portion S1A and S1B whose associated secondary switches SWs1a and SWs2a is not grounded.

During the receive (RX) mode, the receiver RX 20 is connected to the output node S1C on the secondary winding S1. During the RX mode, the TR switches TRSW1 and TRSW2 are optionally used to ground both of the primary winding portions P1A and P1B. Alternatively or in combination, the switches SWp1a and SWp1b are closed to ground the primary winding P1 to prevent any signal from interfering with an echo. To receive an echo signal from one transducer element via either one of the secondary winding portions S1A and S1B, a corresponding one of the secondary switches SWs1a and SWs2a is opened depending on which probe impedance was selected during the TX mode. That is, by closing the secondary switch SWs1a or SWs2a, the associated secondary winding portion is prevented from the echo signal to travel as an input to the receiver 20. At the same time, the other one of the two switches SWs1a and SWs2a is kept open so that the echo signal to travel as an input to the receiver 20. Since the path to the receiver 20 from one transducer element Z11 or Z22 is independently alternated, an echo signal from the other one of the secondary winding portions S1A and S1B does not interfere with the input to the receiver 20.

Figure 9B:
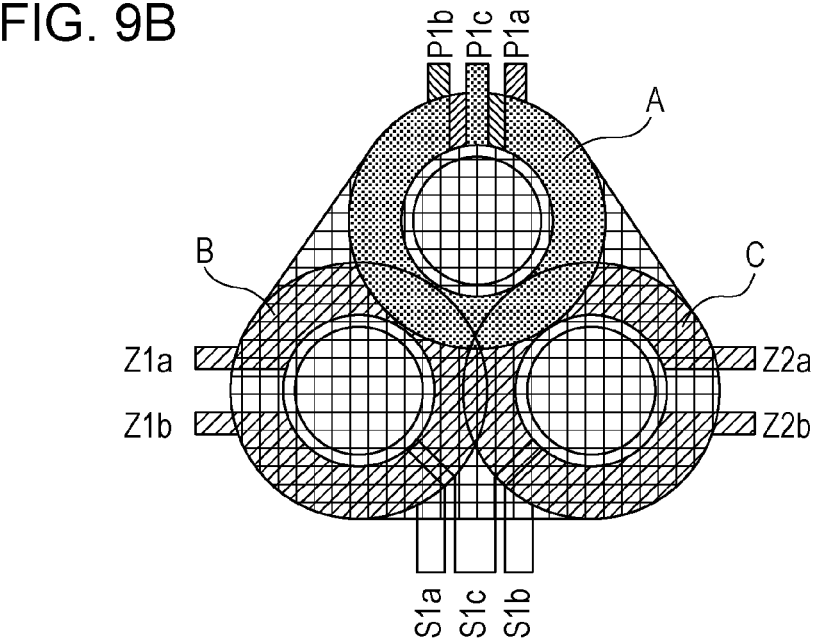
FIG. 9B is a diagram illustrating connections in the transformer-based multiplexer and with the associated components in the eighth embodiment of the ultrasound imaging system according to the current invention.

Now referring to FIG. 9B, a diagram illustrates a cross sectional view of the core of the transformer-based multiplexer in one embodiment of the current invention. On the pole A, the primary winding P1 is placed and has its endings P1a and P1b as well as its tapping point P1c. By the same token, on the pole B, the first shorting winding Z1 is placed and has its endings Z1a and Z1b. On the pole C, the second shorting winding Z2 is placed and has its endings Z2a and Z2b. On one or more of the poles A, B and C, the secondary winding S1 is placed and has its endings S1a and S1b as well as its tapping point S1c. The pole A is located above the poles B and C so that the shorting windings Z1 and Z2 are magnetically isolated with each other. On the other hand, the poles B and C are adjacent to the pole A so that the shorting windings Z1 and Z2 are each magnetically coupled to the primary winding P1. Although the embodiment aligns the poles A, B and C in a triangular geometry, it is not limited to the illustrated configuration.

Figure 10A:
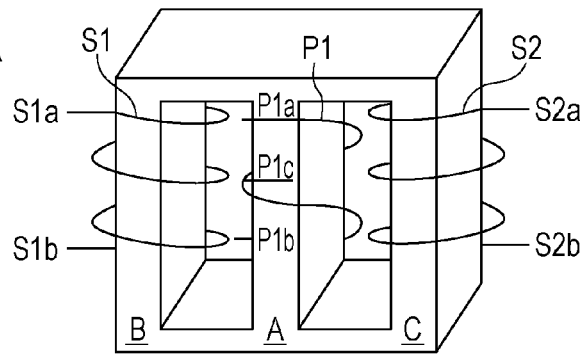
FIG. 10A is a diagram illustrating a transformer core to be used in a ninth embodiment of the multiplexer according to the current invention.

Now referring to FIG. 10A, a diagram illustrating a transformer core to be used in a ninth embodiment of the multiplexer according to the current invention. A primary winding P1 on a first pole A has endings P1a and P1b as well as a tapping terminal P1c. A first secondary winding S1 on a second pole B has endings S1a and S1b and is magnetically coupled with the primary winding P1. A second secondary winding S2 on a third pole C has endings S2a and S2b and is magnetically coupled with the primary winding P1. Although the first secondary winding S1 and the second secondary winding S2 are magnetically associated with the primary winding P1, the first secondary winding S1 and the second secondary winding S2 are not magnetically coupled with each other since the poles B and C are provided in a such manner to prevent magnetic coupling. The relative physical locations of the poles A, B and C are merely conceptual and are not limited to the illustrated relation.

Figure 10B:
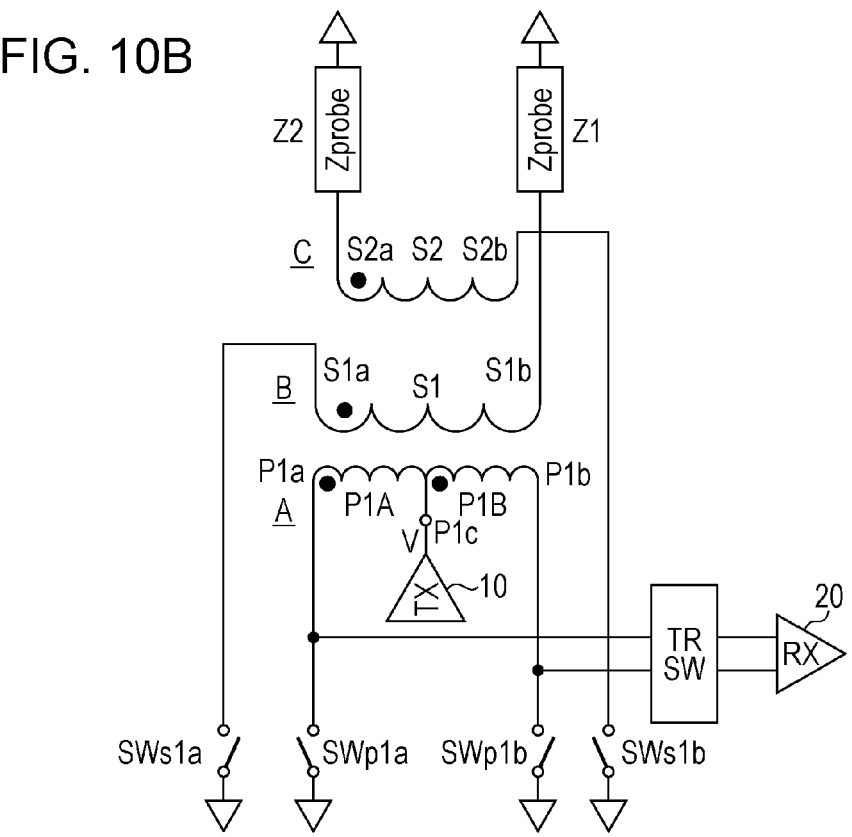
FIG. 10B is a diagram illustrating connections in the transformer-based multiplexer and with the associated components in the ninth embodiment of the ultrasound imaging system according to the current invention.

Now referring to FIG. 10B, a diagram illustrates connections in the transformer-based multiplexer and with the associated components in the ninth embodiment of the ultrasound imaging system according to the current invention. The primary winding P1 on the pole A has two subsections P1A and P1B, and the transmitter TX 10 is tapped in at the terminal P1C between the two subsections P1A and P1B. The primary winding P1 has the terminals P1a and P1b, which are respectively connected to switches SWp1a and SWp1b that are in turn grounded. By turning on and off SWp1a and SWp1b, a pulse is generated according the transmitter signal from the transmitter TX 10. Furthermore, the endings P1a and P1b are connected to a receiver RX 20 via a transmission/receive (TR) switch TRSW.

The first secondary winding S1 on the second pole B has the endings S1a and S1b and is magnetically coupled with the primary winding P1. The ending S1b is connected to Zprobe1 such as a transducer element Z1 while the ending S1a is connected to a first secondary winding switch SWs1a that in turn is grounded. By closing the first secondary winding switch SWs1a during the transmit mode as operationally controlled by the transmit/receive switch TRSW, the first secondary winding S1 no longer sends the pulsed waveforms from the primary winding P1 to the transducer element Z1 since the first secondary winding S1 is grounded at one end.

The second secondary winding S2 on the second pole C has the endings S2a and S2b and is magnetically coupled with the primary winding P1. The ending S2a is connected to Zprobe2 such as a transducer element Z2 while the ending S2b is connected to a second secondary winding switch SWs2a that in turn is grounded. By closing the second secondary winding switch SWs2a during the transmit mode as operationally controlled by the transmit/receive switch TRSW, the second secondary winding S2 no longer sends the pulsed waveforms from the primary winding P1 to the transducer element Z2 since the second secondary winding S2 is grounded at one end.

In the above embodiment of the transformer-based multiplexer, the windings are constructed in a certain manner. Although the first secondary winding S1 and the second secondary winding S2 are magnetically associated with the primary winding P1 in an independent manner, the first secondary winding S1 and the second secondary winding S2 are not magnetically coupled with each other since the poles B and C are provided in a such manner to prevent magnetic coupling. Furthermore, the secondary windings S1 and S2 are electrically isolated from each other for implementing the high-voltage (HV) multiplexer.

The above described ultrasound front-end circuit containing the transformer-based multiplexer has two predetermined modes of operation including transmit (TX) and receive (RX) using the transmission/receive (TR) switch TRSW. When the switches SWp1a and SWp1b are closed, the primary winding P1 is no longer magnetically active. On the other hand, when either of the switches SWp1a and SWp1b is open, the primary winding P1 is magnetically active to couple with the secondary winding S1 and or S2 for transmitting a pulse signal to a transducer element. Thus, by not grounding the primary winding P1, the primary winding P1 functionally switches the front-end circuit into the TX mode. In the RX mode, both of the switches SWp1a and SWp1b are not closed, and the ultrasound front-end circuit generates no pulse signal for outputting to either of the secondary windings S1 and S2.

During the TX mode, by turning on and off the switches SWp1a and SWp1b, a pulsed signal or waveform is generated at the primary winding P1 according to a transmitter signal from the transmitter TX 10 and is outputted through the primary winding P1 to one of the secondary windings S1 and S2 that are selectively coupled to the primary winding P1. During the TX mode, the TR switch TRSW is used to prevent the receiver 20 from receiving any input. Also during the TX mode, the first secondary winding switch SWp1a and the second secondary winding switch SWs2a are used to determine which of Zprobe1 or Zprobe2 impedance is connected via the selected one of the secondary windings S1 and S2 so as to receive the pulsed waveform. That is, either one of the secondary windings S1 and S2 is alternately grounded by closing one of the secondary winding switches SWs1a and SWs2a according to the transmitter signal from the transmitter TX 10. Consequently, the pulsed signal from the primary winding P1 is outputted to Zprobe1 or Zprobe2 at a time via a selected one of the secondary windings S1 and S2 whose associated secondary switches SWs1a and SWs2a is not grounded.

During the receive (RX) mode, the receiver RX 20 is connected to the two independent output nodes via the secondary winding S1 or S2 via the primary winding P1. During the RX mode, no pulse signal is generated according to the transmittal signal from the transmitter 10, and the TR switch TRSW is used to connect the receiver 20 for receiving an input. To receive one echo signal from a transducer element via either one of the secondary windings S1 and S2, a corresponding one of the secondary switches SWs1a and SWs2a is opened depending on which probe impedance was selected during the TX mode. That is, by opening the secondary switches SWs1a and SWs2a, the associated secondary winding has a low impedance path for the echo signal to travel as an input to the receiver 20 via the TR switch TRSW. At the same time, the other one of the two switches SWs1a and SWs2a is optionally kept closed. Since the path to the receiver 20 is independent, an echo signal from the other one of the secondary windings S1 and S2 does not interfere with the input to the receiver 20.

Figure 10C:
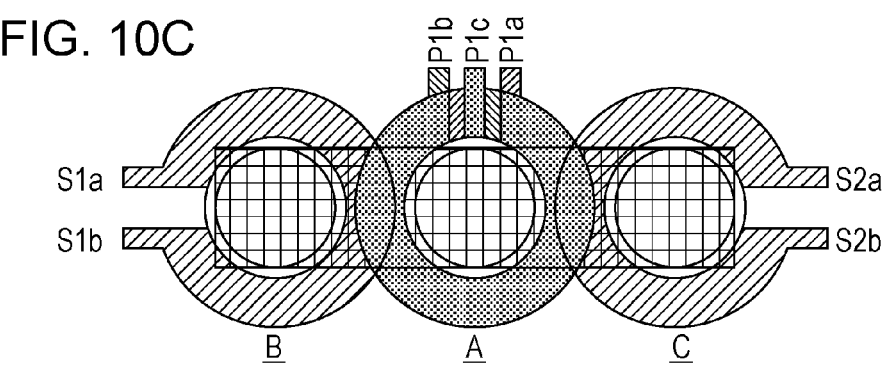
FIG. 10C is a diagram illustrating a cross sectional view of the core of the transformer-based multiplexer in the ninth embodiment of the current invention.

Now referring to FIG. 10C, a diagram illustrates a cross sectional view of the core of the transformer-based multiplexer in one embodiment of the current invention. On the pole A, the primary winding P1 is placed and has its endings P1a and P1b as well as its tapping point P1c. By the same token, on the pole B, the first secondary winding S1 is placed and has its endings S1a and S1b. On the pole C, the second secondary winding S2 is placed and has its endings S2a and S2b. The pole A is located between the poles B and C so that the secondary windings S1 and S2 are magnetically isolated with each other. On the other hand, the poles B and C are adjacent to the pole A so that the secondary windings S1 and S2 are each magnetically coupled to the primary winding P1. Although the embodiment aligns the poles A, B and C in a straight line, it is not limited to the illustrated configuration.

Figure 11A:
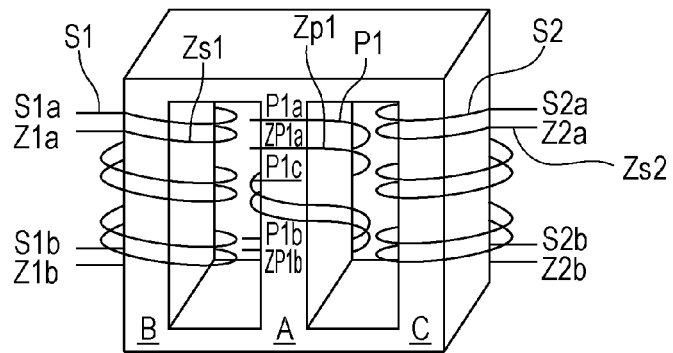
FIG. 11A is a diagram illustrating a transformer core to be used in a tenth embodiment of the multiplexer according to the current invention.

Now referring to FIG. 11A, a diagram illustrating a transformer core to be used in a tenth embodiment of the multiplexer according to the current invention. A primary winding P1 on a first pole A has endings P1a and P1b as well as a tapping terminal P1c. A first shorting winding Zp1 also on the first pole A has endings Zp1a and Zp1b and is magnetically associated with the primary winding P1. A first secondary winding S1 on a second pole B has endings S1a and S1b and is magnetically coupled with the primary winding P1. A first secondary shorting winding Zs1 also on the second pole B is magnetically coupled with the first secondary winding S1 and has endings Z1a and Z1b. A second secondary winding S2 on a third pole C has endings S2a and S2b and is magnetically coupled with the primary winding P1. A second secondary shorting winding Zs2 also on the third pole C is magnetically coupled with the second secondary winding S2 and has endings Z2a and Z2b. Although the first secondary winding S1 and the second secondary winding S2 are magnetically associated with the primary winding P1, the first secondary winding S1 and the second secondary winding S2 are not magnetically coupled with each other since the poles B and C are provided in a such manner to prevent magnetic coupling. The relative physical locations of the poles A, B and C are merely conceptual and are not limited to the illustrated relation.

Figure 11B:
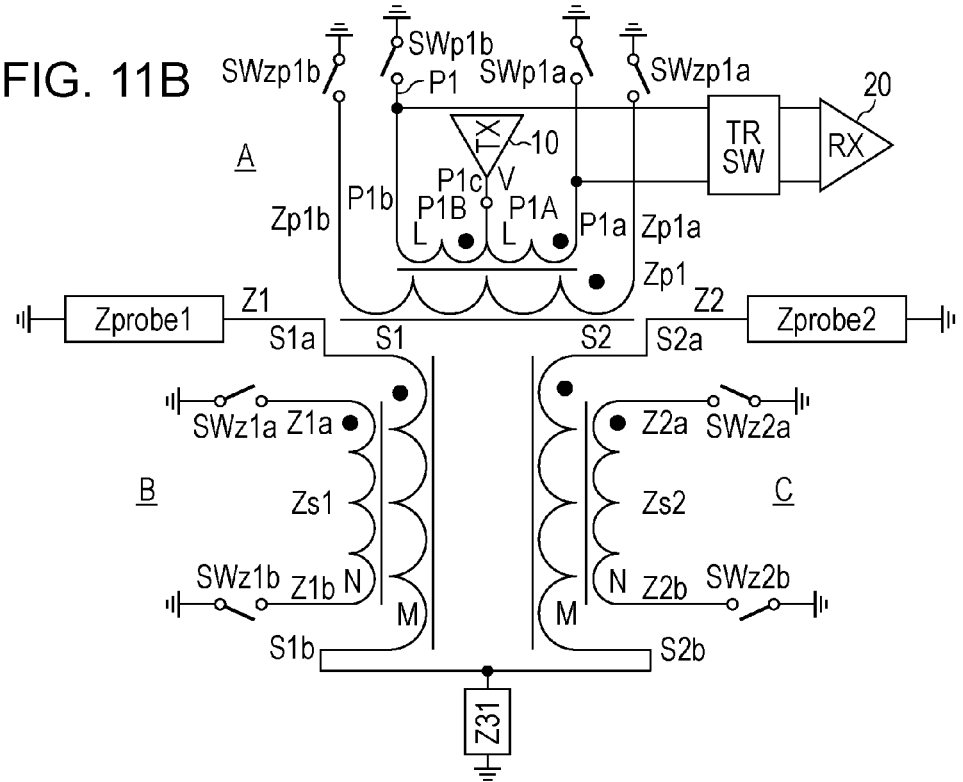
FIG. 11B is a diagram illustrating connections in the transformer-based multiplexer and with the associated components in the tenth embodiment of the ultrasound imaging system according to the current invention.

Now referring to FIG. 11B, a diagram illustrates connections in the transformer-based multiplexer and with the associated components in the ninth embodiment of the ultrasound imaging system according to the current invention. The primary winding P1 and the first shorting winding ZP1 are magnetically coupled on the pole A. The primary winding P1 has two subsections P1A and P1B, and the transmitter TX 10 is tapped in at the terminal P1c between the two subsections P1A and P1B. The primary winding P1 has the terminals P1a and P1b, which are respectively connected to switches SWp1a and SWp1b that are in turn grounded. By turning on and off SWp1a and SWp1b, a pulse is generated according the transmitter signal from the transmitter TX 10. The first shorting winding ZP1 has the terminals Zp1a and Zp1b, which are respectively connected to switches SWzp1a and SWzp1b that are in turn grounded. By closing the switches SWzp1a and SWzp1b, the primary winding P1 is no longer magnetically coupled to other windings as will be later described in detail. Furthermore, the endings P1a and P1b are connected to a receiver RX 20 via a transmission/receive (TR) switch TRSW.

The first secondary winding S1 on the second pole B has the endings S1a and S1b and is magnetically coupled with the primary winding P1. The ending S1a is connected to Zprobe1 such as a transducer element Z1 while the ending S1b is connected to an impedance component Z31. The first secondary shorting winding Zs1 also on the second pole B is magnetically coupled with the first secondary winding S1 and has the endings Z1a and Z1b, which are respectively connected to switches SWz1a and SWz1b that are in turn grounded. By closing the switches SWz1a and SWz1b, the first secondary winding S1 is no longer magnetically coupled to the primary winding P1 and consequently receives none of the pulsed waveforms from the primary winding P1.

The second secondary winding S2 on the second pole C has the endings S2a and S2b and is magnetically coupled with the primary winding P1. The ending S2a is connected to Zprobe2 such as a transducer element Z2 while the ending S1a is connected to the common impedance component Z31. The second secondary shorting winding Zs2 also on the second pole B is magnetically coupled with the second secondary winding S12 and has the endings Z2a and Z2b, which are respectively connected to switches SWz2a and SWz2b that are in turn grounded. By closing the switches SWz2a and SWz2b, the second secondary winding S2 is no longer magnetically coupled to the primary winding P1 and consequently receives none of the pulsed waveforms from the primary winding P1.

In the above embodiment of the transformer-based multiplexer, the windings are constructed in a certain manner. Although the first secondary winding S1 and the second secondary winding S2 are magnetically associated with the primary winding P1 in an independent manner, the first secondary winding S1 and the second secondary winding S2 are not magnetically coupled with each other since the poles B and C are provided in a such manner to prevent magnetic coupling. Furthermore, the secondary windings S1 and S2 are electrically isolated from each other for implementing the high-voltage (HV) multiplexer.

The above described ultrasound front-end circuit containing the transformer-based multiplexer has two predetermined modes of operation including transmit (TX) and receive (RX) using the transmission/receive (TR) switch TRSW. When the switches SWp1a and SWp1b are closed, the primary winding P1 is no longer magnetically active. On the other hand, when either of the switches SWp1a and SWp1b is open, the primary winding P1 is magnetically active to couple with the secondary winding S1 and or S2 for transmitting a pulse signal to a transducer element. Thus, by not grounding the primary winding P1, the primary winding P1 functionally switches the front-end circuit into the TX mode. In the RX mode, both of the switches SWp1a and SWp1b are not closed, and the ultrasound front-end circuit generates no pulse signal for outputting to either of the secondary windings S1 and S2.

The above described ultrasound front-end circuit containing the transformer-based multiplexer has two predetermined modes of operation including transmit (TX) and receive (RX). A transmission/receive (TR) switch is implemented using the switches SWzp1a and SWzp1b in combination with the TR switch TRSW. 60 and the impedance component Z31. When both of the switches SWzp1a and SWzp1b are closed, the first shorting winding Zp1 is grounded and the primary winding P1 is no longer magnetically active. On the other hand, when either of the switches SWzp1a and SWzp1b is open, the first shorting winding Zp1 is not grounded and the primary winding P1 is magnetically active to couple with the first secondary winding S1 and or the second secondary winding S2 for transmitting a pulse signal to a transducer element. Thus, by not grounding the first shorting winding Zp1, the primary winding P1 functionally switches the front-end circuit into the TX mode. In contrast, when both of the switches SWzp1a and SWzp1b are closed, the ultrasound front-end circuit is in the RX mode since no pulse signal is outputted to either of the secondary windings S1/S2 since the primary winding P1 is not magnetically active.

During the TX mode, by turning on and off the switches SWp1a and SWp1b, a pulsed signal or waveform is generated at the primary winding P1 according to a transmitter signal from the transmitter 10 and is outputted through the primary winding P1 to one of the secondary windings S1 and S2 that are selectively coupled to the primary winding P1. Also during the TX mode, the secondary shorting windings Zs1 and Zs2 are used to determine which of Zprobe1 or Zprobe2 impedance is connected via the selected one of the secondary windings S1 and S2 so as to receive the pulsed waveform. That is, either one of the secondary shorting windings Zs1 and Zs2 is alternately grounded by closing only one corresponding pair of the switches SWz2a/SWz2b and the switches SWz1a/SWz1b according to the transmitter signal from the transmitter 10. Consequently, the pulsed signal from the primary winding P1 is outputted to Zprobe1 or Zprobe2 at a time via a selected one of the secondary windings S1 and S2 whose associated secondary shorting winding ZS1 or ZS2 is not grounded.

During the receive (RX) mode, the receiver 20 is selectively connected to the selected one of two output nodes via the TR switch TRSW from the secondary windings S1 and S2. During the receive (RX) mode, the receiver RX 20 is connected to the two independent output nodes via the secondary winding S1 or S2 via the primary winding P1. In addition, during the RX mode, no pulse signal is generated according to the transmittal signal from the transmitter 10, and the TR switch TRSW is used to connect the receiver 20 for receiving an input. To receive one echo signal from a transducer element via either one of the secondary windings S1 and S2, a corresponding one of the two pairs of the switches SWz1a/SWz1b and SWz2a/SWz2b is closed depending on which probe impedance was selected during the TX mode. That is, by shorting the secondary shorting winding ZS1 or ZS2, the associated grounded secondary winding provides a low impedance path for the echo signal to travel as an input to the receiver 20. At the same time, the other one of the two pairs of the switches SWz1a/SWz1b and SWz2a/SWz2b is optionally kept open. An echo signal from the other one of the secondary windings S1 and S2 does not interfere with the input to the receiver 20 since an echo signal from the Zprobe1 or the Zprobe2 is selected at a time along with the impedance components Z31 and Z32 by closing only one of the two pairs of the switches SWz1a/SWz1b and SWz2a/SWz2b. Impedance component Z31 is used to short one side of winding so that a voltage develops across one of the selected secondary windings S1 and S2.

Figure 11C:
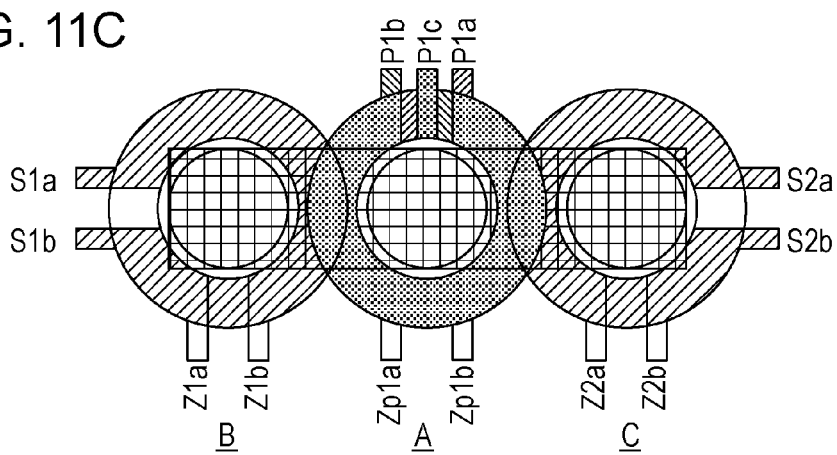
FIG. 11C is a diagram illustrating a cross sectional view of the core of the transformer-based multiplexer in the tenth embodiment of the current invention.

Now referring to FIG. 11C, a diagram illustrates a cross sectional view of the core of the transformer-based multiplexer in one embodiment of the current invention. On the pole A, the primary winding P1 and the first shorting winding Zp1 are placed at a predetermined ratio. The primary winding P1 has its endings P1a and P1b as well as its tapping point P1c while the first shorting winding Zp1 has its endings Zp1a and Zp1b. By the same token, on the pole B, the first secondary winding S1 and the first secondary shorting winding Zs1 are placed at a predetermined ratio. The first secondary winding S1 has its endings S1a and S1b while the first secondary shorting winding Zs1 has its endings Z1a and Z1b. On the pole C, the second secondary winding S2 and the second secondary shorting winding Zs2 are placed at a predetermined ratio. The second secondary winding S2 has its endings S2a and S2b while the second secondary shorting winding Zs2 has its endings Z2a and Z2b. The pole A is located between the poles B and C so that the secondary windings S1 and S2 are magnetically isolated with each other. On the other hand, the poles B and C are adjacent to the pole A so that the secondary windings S1 and S2 are each magnetically coupled to the primary winding P1. Although the embodiment aligns the poles A, B and C in a straight line, it is not limited to the illustrated configuration.

Figure 12:
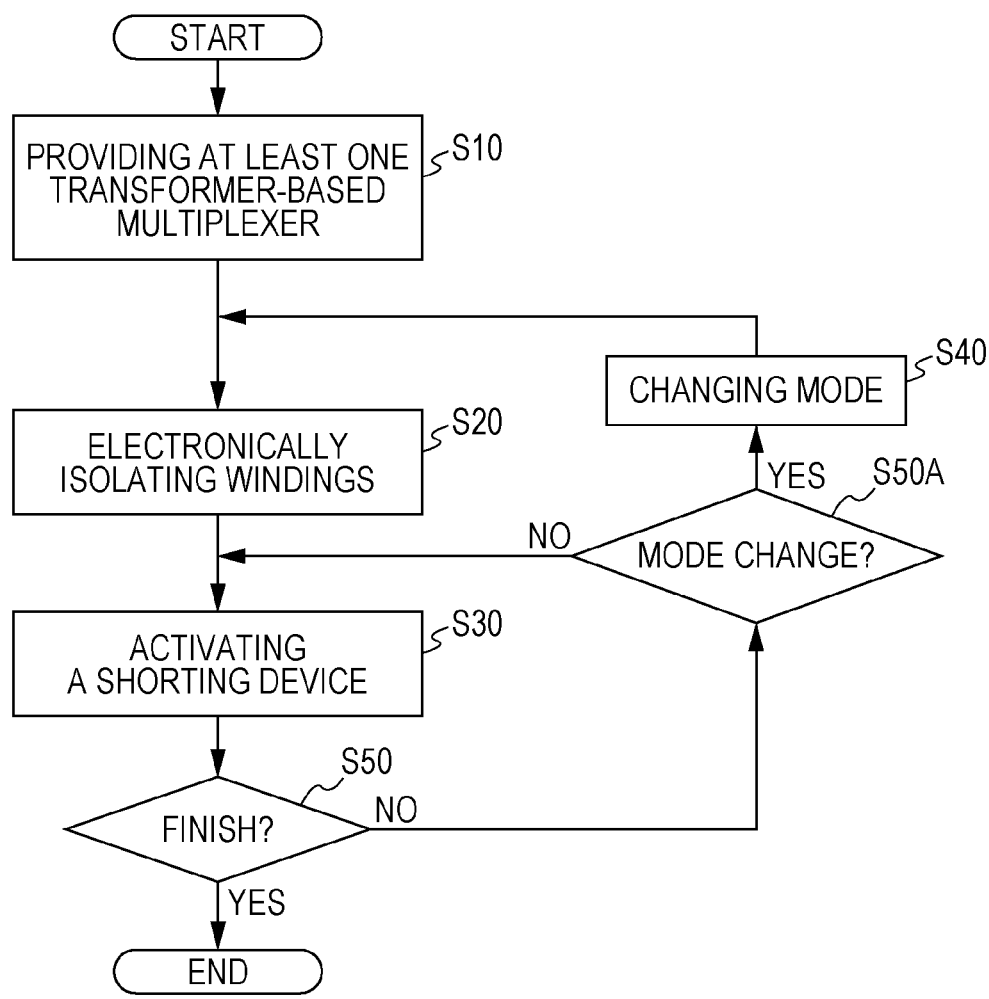
FIG. 12 is a flow chart illustrating steps or acts involved in an embodiment or a process of multiplexing at least two transducer elements using a transfer-based multiplexer in an ultrasound imaging system according to the current invention.

Now referring to FIG. 12, a flow chart illustrates steps or acts involved in an embodiment or a process of multiplexing at least two transducer elements using a transfer-based multiplexer in an ultrasound imaging system according to the current invention. The embodiment includes a step or act of providing at least one transformer-based multiplexer that is connected to at least two transducer elements in a step S10. The transformer-based multiplexer has a first or primary winding connected to the transmitter for sending one of predetermined signals. A second winding is magnetically coupled with the first winding and connected to one of the at least two transducer elements. A third winding is magnetically coupled with the first winding and connected to the other one of the at least two transducer elements. The second and third windings are secondary windings that are magnetically coupled with the primary winding in the above process.

Still referring to FIG. 12, the above provided transformer-based multiplexer accomplishes the following tasks or steps. That is, in a step S20, the second winding is electronically isolated from the first winding while the third winding is electronically isolated from the first winding. At the same time, the third winding is magnetically isolated from the second winding. Subsequently, the above provided transformer-based multiplexer accomplishes in a step S30 the activation of one of a second shorting device associated with the second winding for shoring the second winding and a third shorting device associated with the third winding for shoring the third winding so that one of the two transducer elements is connected at a time. Lastly, it is determined whether or not if the above exemplary process is completed in a step S50. If it is determined that the above exemplary process is completed in the step S50, the process terminates. On the other hand, if is determined that the above exemplary process is not yet completed in the step S50, it is further determined in a step S50A whether or not the current mode of operation should be changed between predetermined modes. If the mode needs to be changed, the above exemplary process performs a mode change step S40 and subsequently proceeds to the step S20. On the other hand, if the mode does not need to be changed, the above exemplary process proceeds to the step S30.

Now referring to FIG. 13, a flow chart illustrates certain steps or acts involved in changing modes in an embodiment or a process of multiplexing at least two transducer elements using a transfer-based multiplexer in an ultrasound imaging system according to the current invention. The embodiment includes a step or act of determining a mode and the steps and acts associated with each of the modes. For example, a step S40A determines in which mode such as transmit or receive the exemplary process operates. If it is determined in the step S40A that the exemplary process operates in the transmit mode, steps 40B, 40C and 40D are performed. That is, a pulse is generated according to a signal from a transmitter in the step 40B, involving a primary winding. In a step S40C, a secondary winding is selected for transmitting the generated pulse. The selected secondary winding is magnetically coupled with the primary winding in the transformer-based multiplexer. Through the primary winding, the generated pulse is sent to the selected secondary winding. Finally, the pulse is transmitted from a transducer element that is connected to the selected secondary winding in the transmit mode.

Still referring to FIG. 13, if it is determined in the step S40A that the exemplary process operates in the receive mode, steps 40E and 40F are performed. That is, the step S40E selects a secondary winding to which an echo signal is sent from a transducer element. Depending upon a receiver configuration, the received echo signal is sent to the selected secondary winding to a predetermined receiver. For example, if the receiver is connected to the primary winding, the received echo signal is sent to the receiver via the primary winding from the selected secondary winding. On the other hand, if the receiver is connected to the secondary winding, the received echo signal is sent from the selected secondary winding to the receiver. In any case, the echo signal is received at the receiver in a step S40F. Finally, it is determined in a step S40G whether or not the above exemplary process has finished. If it is not finished, the exemplary process proceeds back to the step S40A. On the other hand, if it is finished, the exemplary process terminates.

The above embodiments are merely illustrative and not limited to a particular number of the primary or secondary windings in the drawing. The number of windings is optionally expanded in both the secondary winding and the primary winding to a predetermined ratio of N:M where N and M are real numbers. In general, the basic operation of the high-voltage multiplexer is such that the input to the multiplexer is the primary winding and the output of the multiplexer is the secondary winding for the transmitter.

By the same token, the above processes are merely illustrative and not limited to a particular number of the steps or acts in the drawing. The illustrated steps and acts may be performed in combinations and or in different sequences. Furthermore, certain additional steps are optionally performed to achieve certain goals.

In summary, the above specification describes eleven embodiments of the high-voltage transformer-based multiplexer according to the current invention. Three embodiments use a coupled transmit/receive (TR) switches or a coupled shorting winding in combination with the secondary windings. Three other embodiments use high-voltage switches in the secondary windings instead of the coupled transmit/receive (TR) switch or the coupled shorting winding in the secondary windings. In addition, three alternative embodiments includes one embodiment that changes the location of the shorting impedance Z31, another embodiment that replaces the shorting winding with an active TR switch and the third embodiment that changes the position of the receiver (RX) and creates a differential input to the RX block.

It is to be understood, however, that even though numerous characteristics and advantages of the present invention have been set forth in the foregoing description, together with details of the structure and function of the invention, the disclosure is illustrative only, and that although changes may be made in detail, especially in matters of shape, size and arrangement of parts, as well as implementation in software, hardware, or a combination of both, the changes are within the principles of the invention to the full extent indicated by the broad general meaning of the terms in which the appended claims are expressed.

What is claimed is:

1. An ultrasound front-end circuit, comprising:
at least two transducer elements; and
at least one transformer-based multiplexer connected to said at least two transducer elements for selecting one of said at least two transducer elements and sending one of predetermined signals to said selected one of said at least two transducer elements, said transformer-based multiplexer further comprising a core having:
a first winding connected to a transmitter for sending one of the predetermined signals;
a second winding magnetically coupled with said first winding and connected to one of said at least two transducer elements;
a selectively active second shorting device associated with said second winding for shoring said second winding, said second winding being electronically isolated from said first winding;
a third winding magnetically coupled with said first winding and connected to the other one of said at least two transducer elements, said third winding being magnetically isolated from said second winding; and
a selectively active third shorting device associated with said third winding for shoring said third winding, said third winding being electronically isolated from said second winding and said first winding.

2. The ultrasound front-end circuit according to claim 1 wherein said second shorting device is a second shorting winding while said third shorting device is a third shorting winding.

3. The ultrasound front-end circuit according to claim 2 further comprises a first low voltage semiconductor switch for selectively activating said second shorting winding and a second low voltage semiconductor switch for selectively activating said third shorting winding.

4. The ultrasound front-end circuit according to claim 2 further comprises a first active switch for selectively activating said second shorting winding and a second active switch for selectively activating said third shorting winding.

5. The ultrasound front-end circuit according to claim 2 further comprises a first passive switch for selectively activating said second shorting winding and a second passive switch for selectively activating said third shorting winding.

6. The ultrasound front-end circuit according to claim 1 wherein said second shorting device is a second switch while said third shorting device is a third switch.

7. The ultrasound front-end circuit according to claim 1 further comprises at least one receiver connected to said transformer-based multiplexer, said transformer-based multiplexer further comprises a selectively activated first shorting device associated with said first winding for switching between a transmission mode and a reception mode.

8. The ultrasound front-end circuit according to claim 7 wherein said first shorting device is a first shorting winding.

9. The ultrasound front-end circuit according to claim 1 further comprises at least one receiver connected to said transformer-based multiplexer, said second shorting device is a second switch for switching between a transmission mode and a reception mode while said third shorting device is a third switch for switching between the transmission mode and the reception mode.

10. The ultrasound front-end circuit according to claim 7 wherein said first shorting device is a first switch.

11. The ultrasound front-end circuit according to claim 7 further comprises a multiplexer connected between said transformer-based multiplexer and said at least one receiver for selecting said second winding and said third winding for an input signal to said at least one receiver.

12. The ultrasound front-end circuit according to claim 1 further comprises a first receiver connected to said second winding and a second receiver connected to said third winding.

13. The ultrasound front-end circuit according to claim 1 wherein one end said second winding is connected to one end of said third winding.

14. The ultrasound front-end circuit according to claim 1 further comprises at least a one transmitter connected to said transformer-based multiplexer for generating the predetermined signal and outputting the predetermined signal to said transformer-based multiplexer.

15. The ultrasound front-end circuit according to claim 1 wherein said transformer-based multiplexer is operationally connected to at least one transmitter located in a diagnostic unit, said at least one transmitter generating the predetermined signal and outputting the predetermined signal to said transformer-based multiplexer.

16. The ultrasound front-end circuit according to claim 1 further comprises one receiver connected to said first winding, said second shorting device switching between a transmission mode and a reception mode while said third shorting device switching between the transmission mode and the reception mode.

17. The ultrasound front-end circuit according to claim 1 further comprises one receiver connected to said first winding and a selectively activated first shorting device associated with said first winding for switching between a transmission mode and a reception mode.

18. An ultrasound diagnostic system, comprising:
a probe including at least two transducer elements; and
at least one transformer-based multiplexer connected to said at least two transducer elements for selecting one of said at least two transducer elements and sending a predetermined signal to said selected one of said at least two transducer elements; and
at least a one transmitter connected to said transformer-based multiplexer for generating and outputting the predetermined signal.

19. The ultrasound diagnostic system according to claim 18 wherein said at least one transmitter is located in said probe.

20. The ultrasound diagnostic system according to claim 18 wherein said at least one transmitter is located in a diagnostic unit.

21. A method of multiplexing at least two transducer elements, comprising:
providing at least one transformer-based multiplexer connected to at least two transducer elements, the one transformer-based multiplexer having a first winding connected to the transmitter for sending one of predetermined signals, a second winding magnetically coupled with the first winding and connected to one of the at least two transducer elements, a third winding magnetically coupled with the first winding and connected to the other one of said at least two transducer elements;
electronically isolating the second winding from the first winding;
electronically isolating the third winding from the first winding;
magnetically isolating the third winding isolated from the second winding;
activating one of a second shorting device associated with the second winding for shoring the second winding and a third shorting device associated with the third winding for shoring the third winding.

22. The method of multiplexing at least two transducer elements according to claim 21 wherein the second shorting device utilizes a second shorting winding while the third shorting device utilizes a third shorting winding.

23. The method of multiplexing at least two transducer elements according to claim 21 wherein said activating step utilizes a first active switch for selectively activating the second shorting winding and a second active switch for selectively activating the third shorting winding.

24. The method of multiplexing at least two transducer elements according to claim 21 wherein said activating step utilizes a first passive switch for selectively activating the second shorting winding and a second passive switch for selectively activating the third shorting winding.

25. The method of multiplexing at least two transducer elements according to claim 21 wherein the second shorting device utilizes a second switch while the third shorting device utilizes a third switch.

26. The method of multiplexing at least two transducer elements according to claim 21 wherein the transformer-based multiplexer selectively activates a first shorting device associated with the first winding for switching between a transmission mode and a reception mode.

27. The method of multiplexing at least two transducer elements according to claim 25 wherein the first shorting device utilizes a first shorting winding.

28. The method of multiplexing at least two transducer elements according to claim 25 wherein the first shorting device utilizes a first switch.

* * * * *